(12) United States Patent
Peyser et al.

(10) Patent No.: US 7,725,149 B2
(45) Date of Patent: May 25, 2010

(54) DEVICES, METHODS, AND KITS FOR NON-INVASIVE GLUCOSE MEASUREMENT

(76) Inventors: Thomas A. Peyser, 2030 Gordon Ave., Menlo Park, CA (US) 94025; Russell O. Potts, 76 Uranus Ter., San Francisco, CA (US) 94114; Herbert L. Berman, 12680 Viscaino Rd., Los Altos Hills, CA (US) 94022; James W. Moyer, 4281 23rd St., San Francisco, CA (US) 94114; Mikhail A. Kouchnir, 980 Belmont Ter., Apt. 5, Sunnyvale, CA (US) 94086

( * ) Notice: Subject to any disclaimer, the term of this patent is extended or adjusted under 35 U.S.C. 154(b) by 1223 days.

(21) Appl. No.: 11/159,587

(22) Filed: Jun. 22, 2005
(Under 37 CFR 1.47)

(65) Prior Publication Data
US 2006/0004271 A1    Jan. 5, 2006

Related U.S. Application Data

(60) Provisional application No. 60/585,414, filed on Jul. 1, 2004.

(51) Int. Cl.
A61B 5/05        (2006.01)
A61B 5/00        (2006.01)
(52) U.S. Cl. ..................... 600/346; 600/362
(58) Field of Classification Search ............... 600/362, 600/346, 347, 365
See application file for complete search history.

(56) References Cited

U.S. PATENT DOCUMENTS 3,551,554 A    12/1970   Herschler
4,444,193 A *  4/1984    Fogt et al. ............... 600/362

(Continued)

FOREIGN PATENT DOCUMENTS

EP          0 304 304 A2    2/1989

(Continued)

OTHER PUBLICATIONS

International Search Report mailed Mar. 21, 2006, for PCT Application No. PCT/US2005/022139 filed Jun. 22, 2005, six pages.

(Continued)

*Primary Examiner*—Charles A Marmor, II
*Assistant Examiner*—Christian Y Jang

(57) ABSTRACT

Described are devices, methods, and kits for non-invasively measuring glucose. In general, the devices comprise skin patches for placement on a skin surface and measurement devices for measuring glucose collected in the patches. The patches may include an adhesive material, a collection layer, an interface layer, and a sweat-permeable membrane. The sweat-permeable membrane is configured to act as a barrier to epidermal contaminants and glucose brought to the skin surface via diffusion. In this way, non-correlatable skin surface glucose will not be measured. The patches may further include components to induce a local sweat response. The measurement device typically includes a display, a processor, and a measurement mechanism. The methods typically include the steps of wiping the skin surface with a wipe containing at least one solvent for removing glucose, placing a patch on a skin surface, and measuring glucose collected in the patch. Kits comprising the patch and measurement device are also described.

24 Claims, 16 Drawing Sheets

U.S. PATENT DOCUMENTS

| | | | |
|---|---|---|---|
| 4,821,733 | A | 4/1989 | Peck |
| 5,036,861 | A | 8/1991 | Sembrowich et al. |
| 5,140,985 | A | 8/1992 | Schroeder et al. |
| 5,306,861 | A | 4/1994 | Amos et al. |
| 5,443,080 | A * | 8/1995 | D'Angelo et al. ............ 600/573 |
| 5,465,713 | A * | 11/1995 | Schoendorfer .............. 600/346 |
| 5,638,815 | A | 6/1997 | Schoendorfer |
| 5,849,174 | A * | 12/1998 | Sanghera et al. ......... 205/777.5 |
| 5,954,685 | A * | 9/1999 | Tierney ........................ 604/20 |
| 6,117,290 | A | 9/2000 | Say et al. |
| 6,128,519 | A | 10/2000 | Say |
| 6,180,052 | B1 | 1/2001 | Ouellette et al. |
| 6,214,206 | B1 | 4/2001 | Kriz |
| 6,464,849 | B1 | 10/2002 | Say et al. |
| 6,479,015 | B1 * | 11/2002 | Long et al. .................... 422/58 |
| 6,503,198 | B1 | 1/2003 | Aronowtiz et al. |
| 6,706,160 | B2 | 3/2004 | Kriz |
| 6,750,311 | B1 | 6/2004 | Van Antwerp et al. |
| 7,310,544 | B2 | 12/2007 | Brister et al. |
| 7,381,184 | B2 | 6/2008 | Funderburk et al. |
| 2002/0004640 | A1 * | 1/2002 | Conn et al. .................... 604/20 |
| 2002/0095073 | A1 | 7/2002 | Jacobs et al. |
| 2002/0128578 | A1 * | 9/2002 | Johnston et al. ............... 602/43 |
| 2002/0169394 | A1 * | 11/2002 | Eppstein et al. ............. 600/573 |
| 2003/0215487 | A1 * | 11/2003 | Kim et al. .................... 424/449 |
| 2004/0098009 | A1 | 5/2004 | Boecker et al. |
| 2004/0102803 | A1 | 5/2004 | Boecker et al. |
| 2004/0171980 | A1 | 9/2004 | Mitragotri et al. |
| 2004/0214492 | A1 | 10/2004 | Martz |
| 2004/0236244 | A1 * | 11/2004 | Allen et al. ................. 600/532 |
| 2004/0242976 | A1 * | 12/2004 | Abreu ........................ 600/315 |
| 2005/0009101 | A1 | 1/2005 | Blackburn |
| 2005/0023445 | A1 * | 2/2005 | Horn et al. .............. 250/214 R |
| 2005/0182307 | A1 | 8/2005 | Currie et al. |
| 2005/0197554 | A1 | 9/2005 | Polcha |
| 2005/0238537 | A1 | 10/2005 | Say et al. |
| 2006/0036139 | A1 | 2/2006 | Brister et al. |
| 2006/0036145 | A1 | 2/2006 | Brister et al. |
| 2007/0027381 | A1 | 2/2007 | Stafford |
| 2007/0027383 | A1 | 2/2007 | Peyser et al. |
| 2007/0078321 | A1 | 4/2007 | Mazza et al. |
| 2007/0078322 | A1 | 4/2007 | Stafford |
| 2007/0179371 | A1 | 8/2007 | Peyser et al. |
| 2007/0179373 | A1 | 8/2007 | Pronovost |
| 2007/0191700 | A1 | 8/2007 | Say et al. |
| 2008/0004512 | A1 | 1/2008 | Funderburk et al. |
| 2008/0064941 | A1 | 3/2008 | Funderburk et al. |
| 2008/0071156 | A1 | 3/2008 | Brister et al. |
| 2008/0124663 | A1 | 5/2008 | Anderson et al. |

FOREIGN PATENT DOCUMENTS

| | | |
|---|---|---|
| EP | 0 304 304 A3 | 2/1989 |
| EP | 0 304 304 B1 | 2/1989 |
| JP | 2006-250949 A | 9/2006 |
| WO | WO-99/17114 A1 | 4/1999 |
| WO | WO-99/45140 A1 | 9/1999 |
| WO | WO-00/35340 A1 | 6/2000 |
| WO | WO-01/25474 A2 | 4/2001 |
| WO | WO-01/25474 A3 | 4/2001 |
| WO | WO-03/015636 A1 | 2/2003 |
| WO | WO-2006/007472 A2 | 1/2006 |

OTHER PUBLICATIONS

Boysen, T.C. et al. (May 1984). "A Modified Anaerobic Method of Sweat Collection," *Journal of Applied Physiology* 56(5):1302-1307.

Cunningham, D.D. et al. (2003). "Measurements of Glucose on the Skin Surface, in Stratum Corneum and in Transcutaneous Extracts: Implications for Physiological Sampling," *Clin. Chem. Lab. Med.* 41(9):1224-1228.

Falasca, A. et al. (1979). "Purification and Partial Characterization of a Mitogenic Lectin from *Vicia sativa*," *Biochim. Biophys.Acta.* 577:71-81.

James, T.D. et al. (1994). "Novel Photoinduced Electron-Transfer Sensor for Saccharides Based on the Interaction of Boronic Acid and Amine," *J. Chem. Soc. Chem. Commun.* 4:477-478.

James, T.D. et al. (Mar. 23, 1995). "Chiral Discrimination of Monosaccharides Using a Fluorescent Molecular Sensor," *Nature* 374:345-347.

Kriz, D. et al. (1998). "SIRE-Technology. Part I. Amperometric Biosensor Based on Flow Injection of the Recognition Element and Differential Measurements," *Instrumentation Science & Technology* 26(1):45-57.

Nadel, E.R. et al. (Nov. 1973). "Effect of Skin Wettedness on Sweat Gland Response," *J. Appl. Physiol.* 35(5):689-694.

Nakashima, K. et al. (Jul. 1994). "Sugar-Assisted Chirality Control of Tris(2,2'-bipyridine)-Metal Complexes," *Chem. Lett.* 7:1267-1270.

Rao, G. et al. (Dec. 1995). "Reverse Iontophoresis: Noninvasive Glucose Monitoring in Vivo in Humans," *Pharm. Res.* 12(12):1869-1873.

Sato, K. et al. (1970). "Regional and Individual Variations in the Function of the Human Eccrine Sweat Gland," *J. Invest. Dermat.* 54(6):443-449.

Yoon, J. et al. (1992). "Fluorescent Chemosensors of Carbohydrates. A Means of Chemically Communicating the Binding of Polyols in Water Based on Chelation-Enhanced Quenching," *J. Am. Chem. Soc.* 114:5874-5875.

International Search Report mailed on Oct. 26, 2007, for PCT Application No. PCT/US2007/013392, filed on Jun. 6, 2007, six pages.

Non-Final Office Action mailed on Mar. 19, 2009, for U.S. Appl. No. 11/451,738, filed Jun. 12, 2006, eleven pages.

Non-Final Office Action mailed on Mar. 11, 2009, for U.S. Appl. No. 11/528,750, filed Sep. 27, 2006, nine pages.

Chuang, Y-J. et al. (2007). "A Spontaneous and Passive Waste-management Device (PWMD) for a Micro Direct Methanol Fuel Cell," *J. Micromech. Microeng.* 17:915-922.

International Preliminary Report on Patentability mailed Dec. 31, 2008, for PCT Application No. PCT/US2007/013392, filed Jun. 6, 2007, eight pages.

International Search Report mailed Oct. 29, 2008, for PCT Application No. PCT/US2008/007932 filed Jun. 25, 2008, seven pages.

Lam, P. et al. (2002). "Surface-tension-confined Microfluidics," *Langmuir* 18(3):948-951.

Non-Final Office Action mailed on Nov. 12, 2008, for U.S. Appl. No. 11/159,587, filed Jun. 22, 2005, 14 pages.

Yao, S-C. et al. (2006). "Micro-electro-mechanical Systems (MEMS)-based Micro-scale Direct Methanol Fuel Cell Development," *Energy* 31:636-649.

Yasuda, T. et al. (2003). "Automatic Transportation of a Droplet on a Wettability Gradient Surface," *The 7th International Conference on Miniaturized Chemical and Biochemical Analysis Systems*, Squaw Valley, CA, Oct. 5-9, 2003, pp. 1129-1132, available at <http://www.chem.ualberta.ca/~microtas/Volume2/065-121.pdf>, last visited Jan. 13, 2009, four pages.

Yasuda, T. et al. (2003). "Droplet Transportation Induced by a Gradient in Surface Free Energy," *Proceedings of the 20th Sensor Symposium* 20:249-252.

Zhao, B. et al. (Feb. 9, 2001). "Surface-directed Liquid Flow Inside Microchannels," *Science* 291:1023-1026.

Aussedat, B. et al. (2000). "Interstitial Glucose Concentration and Glycemia: Implications for Continuous Subcutaneous Glucose Monitoring," *Am. J. Physiol. Endocrinol. Metab.* 278:E716-E728.

CDC. (Jun. 18, 2008). "2007 National Diabetes Fact Sheet," located at <http://www.cdc.gov.diabetes/pubs/factsheet07.htm>, last visited on Sep. 9, 2009, three pages.

CDC. (2007). "National Diabetes Fact Sheet, 2007," located at <http://www.cdc.gov.diabetes/pubs/factsheet07.htm>, last visited on Sep. 9, 2009, fourteen pages.

Coury, A.J. (1983). "Development of a Screening System for Cystic Fibrosis" *Clinical Chemistry* 29(9):1593-1597.

Final Office Action mailed on Oct. 14, 2009, for U.S. Appl. No. 11/451,738, filed Jun. 12, 2006, eleven pages.

Final Office Action mailed on Oct. 9, 2009, for U.S. Appl. No. 11/528,750, filed Sep. 27, 2006, nine pages.

Khalil, O.S. (2004). "Non-Invasive Glucose Measurement Technologies: An Update from 1999 to the Dawn of the New Millennium," *Diabetes Technology & Therapeutics* 6(5):660-697.

Lasker, R.D. (1993). "The Diabetes Control and Complications Trial," *N Engl J Med* 329(14)1035-1036.

Lobitz, W.C. et al. (1948). "Chemistry of Palmar Sweat. III. Reducing Substances" *Arch. Dermatol. & Syph.* 57:819-826.

Morenkova, S.A. (Sep. 29, 2004). "Noninvasive Method of Diagnostics of the Diabetes," *Klin Lab Diagn* 3:14-15. (English Machine Translation Included.).

Rothman, S. (1954). "Composition of Eccrine Sweat and Aqueous Surface Film," in *Physiology and Biochemistry of the Skin*, The University of, Chicago Press, Chicago, IL, pp. 209-220.

Silvers, S. et al. (1928). "Simultaneous Study of the Constituents of the Sweat, Urine, Blood, Also Gastric Acidity and Other Manifestations Resulting From Sweating", *Am. J. Physiol* 84:577-582.

Tamada, J.A. et al. (Nov. 17, 1999). "Noninvasive Glucose Monitoring: Comprehensive Clinical Results.," *JAMA* 282(19):1839-1844.

Wantanabe, Y. et al. (1986). "A Study of the Dynamics of Glucose in Sweat by High Performance Liquid Chromatography", *Clinical Chemistry* 15(2):75-79.

Written Opinion mailed on Mar. 21, 2006, for PCT Application No. PCT/US2005/022139 filed on Jun. 22, 2005, nine pages.

Written Opinion mailed on mailed on Oct. 26, 2007, for PCT Application No. PCT/US2007/013392, filed on Jun. 6, 2007, seven pages.

Written Opinion mailed on mailed Oct. 29, 2008, for PCT Application No. PCT/US2008/007932 filed Jun. 25, 2008, seven pages.

\* cited by examiner

DEVICES, METHODS, AND KITS FOR NON-INVASIVE GLUCOSE MEASUREMENT

CROSS REFERENCE TO RELATED APPLICATIONS

This application claims priority to U.S. Ser. No. 60/585,414 filed on Jul. 1, 2004, which is hereby incorporated by reference in its entirety.

FIELD

The devices, methods, and kits described here are in the field of non-invasive glucose measurement, and more specifically, non-invasive measurement of nanogram quantities of glucose, which have come to the skin surface via sweat.

BACKGROUND

The American Diabetes Association reports that approximately 6% of the population in the United States, a group of 16 million people, has diabetes, and that this number is growing at a rate of 12-15% per annum. The Association further reports that diabetes is the seventh leading cause of death in the United States, contributing to nearly 200,000 deaths per year. Diabetes is a life-threatening disease with broad complications, which include blindness, kidney disease, nerve disease, heart disease, amputation and stroke. Diabetes is believed to be the leading cause of new cases of blindness in individuals aging between 20 and 74; approximately 12,000-24,000 people per year lose their sight because of diabetes. Diabetes is also the leading cause of end-stage renal disease, accounting for nearly 40% of new cases. Nearly 60-70% of people with diabetes have mild to severe forms of diabetic nerve damage which, in severe forms, can lead to lower limb amputations. People with diabetes are 2-4 times more likely to have heart disease and to suffer strokes.

Diabetes results from the inability of the body to produce or properly use insulin, a hormone needed to convert sugar, starches, and the like into energy. Although the cause of diabetes is not completely understood, genetics, environmental factors, and viral causes have been partially identified.

There are two major types of diabetes: Type 1 and Type 2. Type 1 diabetes (also known as juvenile diabetes) is caused by an autoimmune process destroying the beta cells that secrete insulin in the pancreas. Type 1 diabetes most often occurs in young adults and children. People with Type 1 diabetes must take daily insulin injections to stay alive.

Type 2 diabetes is a metabolic disorder resulting from the body's inability to make enough, or properly to use, insulin. Type 2 diabetes is more common, accounting for 90-95% of diabetes. In the United States, Type 2 diabetes is nearing epidemic proportions, principally due to an increased number of older Americans and a greater prevalence of obesity and sedentary lifestyles.

Insulin, in simple terms, is the hormone that allows glucose to enter cells and feed them. In diabetics, glucose cannot enter the cells, so glucose builds up in the blood to toxic levels.

Diabetics having Type 1 diabetes are typically required to self-administer insulin using, e.g., a syringe or a pen with needle and cartridge. Continuous subcutaneous insulin infusion via external or implanted pumps is also available. Diabetics having Type 2 diabetes are typically treated with changes in diet and exercise, as well as with oral medications. Many Type 2 diabetics become insulin-dependent at later stages of the disease. Diabetics using insulin to help regulate their blood sugar levels are at an increased risk for medically-dangerous episodes of low blood sugar due to errors in insulin administration, or unanticipated changes in insulin absorption.

It is highly recommended by the medical profession that insulin-using patients practice self-monitoring of blood glucose ("SMBG"). Based upon the level of glucose in the blood, individuals may make insulin dosage adjustments before injection. Adjustments are necessary since blood glucose levels vary day to day for a variety of reasons, e.g., exercise, stress, rates of food absorption, types of food, hormonal changes (pregnancy, puberty, etc.) and the like. Despite the importance of SMBG, several studies have found that the proportion of individuals who self-monitor at least once a day significantly declines with age. This decrease is likely due simply to the fact that the typical, most widely used, method of SMBG involves obtaining blood from a capillary finger stick. Many patients consider obtaining blood to be significantly more painful than the self-administration of insulin.

Non- or minimally-invasive techniques are being investigated, some of which are beginning to focus on the measurement of glucose on the skin surface or in interstitial fluid. For example, U.S. Pat. No. 4,821,733 to Peck describes a process to detect an analyte that has come to the skin surface via diffusion. Specifically, Peck teaches a transdermal detection system for the detection of an analyte that migrates to the skin surface of a subject by diffusion in the absence of a liquid transport medium, such as sweat. As will be described in more detail below, because the process of passive diffusion of an analyte to the skin surface takes an unreasonably long period of time (e.g., a few hours to several days), Peck does not provide a practical non-invasive glucose monitoring solution.

Similarly, U.S. Pat. No. 6,503,198 to Aronowitz et al. ("Aronowitz") describes a transdermal system for analyte extraction from interstitial fluid. Specifically, Aronowitz teaches patches containing wet and dry chemistry components. The wet component is used to form a gel layer for the extraction and liquid bridge transfer of the analyte from the biological fluid to the dry chemistry component. The dry chemistry component is used to quantitatively or qualitatively measure the analyte. One disadvantage of the system described in Aronowitz is the effect of a wet chemistry interface in providing a liquid phase environment on the skin in which different sources of glucose could be irreversibly mixed with one another. A liquid phase contact with the skin surface could make it impossible to distinguish between glucose on the skin surface originating from many day old epidermal debris, glucose on the skin surface originating from many hours old transdermal diffusion, and finally, glucose on the skin from the more timely output of the eccrine sweat gland.

Others have investigated glucose measurement in sweat; however, they have failed to demonstrate a correlation between blood glucose levels and sweat glucose levels, and have similarly failed to establish or demonstrate that only glucose coming from sweat is being measured. For example, U.S. Pat. No. 5,140,985 to Schroeder et al. ("Schroeder") describes a non-invasive glucose monitoring unit, which uses a wick to absorb the sweat and electrochemistry to make glucose measurements. Schroeder relies on an article by T. C. Boysen, Shigeree Yanagaun, Fusaho Sato and Uingo Sato published in 1984 in the *Journal of Applied Psychology* to establish the correlation between blood glucose and sweat glucose levels, but quantitative analysis of the data provided therein demonstrates that the blood glucose and sweat glucose levels of the two subjects described there cannot be correlated (yielding correlation coefficients of approximately 0.666 and 0.217 respectively). Additional methods must be used, beyond those cited in the paper by Boysen et al., to isolate the glucose in sweat from other sources of glucose on the skin.

Similarly, U.S. Pat. No. 5,036,861 to Sembrowich et al. ("Sembrowich") describes glucose monitoring technology based on analyzing glucose on the skin surface from a localized, modified sweat response. In a like manner, U.S. Pat. No. 5,638,815 to Schoendorfer ("Schoendorfer") describes a dermal patch to be worn on the skin for increasing the concentration of an analyte expressed through the skin in perspiration, to a conveniently measurable level. However, similar to Schroeder, Sembrowich and Schoendorfer each fail to teach or describe methods or steps for isolating or distinguishing the glucose in sweat from other confounding sources of glucose found on the skin surface.

BRIEF SUMMARY

Described here are devices, methods, and kits for non-invasive glucose measurement. In general, the devices comprise skin patches configured to collect sweat and which allow for the measurement of glucose, and a corresponding measurement device. In one variation, the skin patch comprises an adhesive material, a sweat-permeable membrane, a collection layer, a detector configured to detect glucose, and an interface layer. In another variation, the skin patch comprises a sweat collection reservoir configured to collect glucose that has come to the skin surface via sweat, and a glucose detector capable of detecting nanogram quantities of glucose, wherein the patch is configured to operate with a measurement device for measuring the glucose.

In some variations, the detector is an electrochemical-based detector, in other variations the detector is a fluorescent-based detector. The sweat-permeable membrane is configured to act as a barrier to epidermal contaminants and glucose brought to the skin surface via diffusion. In some variations, the sweat-permeable membrane comprises a material that is generally occlusive, but allows sweat to pass therethrough. In other variations, the sweat-permeable membrane comprises a liquid polymer that cures when exposed to oxygen, leaving openings only over the sweat gland pores. The sweat-permeable membrane may also comprise a solid polymer, or inorganic material with micropores. The sweat-permeable membrane and the adhesive material may be in a single layer, or may be in separate distinct layers.

The patch may further comprise a backing layer, or a release liner. In some variations, the backing layer comprises a water vapor-impermeable, occlusive material. The collection layer may comprise a fixed volume reservoir to help minimize the confounding effect of a variable sweat rate. In some variations, the patch comprises an electrical circuit, at least one conductor, or an optical transmission pathway to determine that the fixed volume reservoir is filled.

Depending on the nature of the glucose detector, the interface layer of the patch may comprise materials required for the operation of an electrochemical detector or it may be optically transmissive. For example, when the glucose detector is fluorescent-based, the interface layer is typically transparent to the excitation and emission wavelength of the fluorescent-based detector. Similarly, when the glucose detector is electrochemical-based, the interface layer typically comprises at least two electrodes.

The patch may further comprise a physical, chemical, or mechanical mechanism of inducing a local sweat response. For example, the patch may comprise pilocarpine, alone, with a permeation enhancer, or configured for iontophoretic delivery. Similarly, the patch may comprise a chemical capable of inducing a local temperature increase, thereby initiating a local sweat response. In a like manner, the patch may also comprise a heater for sufficient localized heating of the skin surface to induce an enhanced local sweat response.

Glucose measurement devices for use with a skin patch are also described. Typically, the glucose measurement device comprises a display, a processor, computer executable code for executing a calibration algorithm, and an ultra-sensitive measurement mechanism for measuring glucose collected in a corresponding patch. The measurement mechanism is configured to measure nanogram quantities of glucose. The glucose measurement device may also comprise a power supply, memory, a link to download data to a computer, and combinations thereof. The measurement device may also comprise a pressure-inducer to express sweat fluid from the sweat gland lumen and help provide a more suitable amount of sweat on the skin surface. The measurement device may also comprise an iontophoretic source for use in driving pilocarpine, or other suitable molecules, into the skin resulting in a pharmacologically-enhanced local sweat rate.

In variations where the glucose detector is fluorescent-based, the measurement mechanism typically comprises a suitably optimized optical source and a detector. The optical source may be an appropriately-tuned, narrow bandpass optical source such as a light-emitting diode (LED) centered at the excitation wavelength of the fluorescent molecule, or may be a broader optical source having a bandpass filter at the excitation wavelength of the fluorescent molecule. The optical detector typically comprises a photodetector having a bandpass filter at the emission wavelength of the fluorescent molecule. In variations where the glucose detector is electrochemical-based, the measurement device typically provides a contact mechanism for establishment of an electrical contact with the patch.

The measurement device may also be configured to detect a marker left on the skin surface. For example, an optical source and detector may be included to detect the presence of a separate non-interfering fluorescent molecule associated with the proper use of a skin cleaning wipe, which is typically required to enable the measurement. The measurement device may thereby determine that no marker has been detected on the skin surface and therefore that any attempt to correlate the skin surface glucose with blood glucose could be contaminated by food residues or other non-correlatable sources of glucose. The measurement device may also be configured to provide an indication of a condition to a user. The condition may be, for example, the user's glucose concentration being either dangerously low, or dangerously high. The measurement device may provide such an indication using sounds, lights, word prompts, or combinations thereof.

Methods of measuring glucose on the skin are also described herein. These methods may comprise the steps of wiping a skin surface with a wipe containing at least one solvent for removing glucose, placing a patch on the skin surface, wherein the patch comprises a sweat-permeable membrane configured to act as a barrier to epidermal contaminants and glucose brought to the skin surface via diffusion, and measuring glucose collected in the patch.

The patch may be placed on any suitable skin surface, e.g., an anatomical site that is convenient to the user for purposes of glucose monitoring and which produces a satisfactory sweat response with or without stimulation. In some variations, the patch is placed on the volar fingertip. In some variations, the step of placing a patch on the skin surface occurs from about 10 seconds to about 2 minutes after the step of wiping the skin surface.

Glucose measurement kits are also provided. In some variations the kits comprise at least one patch, either alone, or in combination with instructions on using the patch. The kits may also comprise a patch and a measurement device, or combinations of different patches. Typically, the patches are individually wrapped or packaged and are disposable and configured for a single use.

DETAILED DESCRIPTION

Described herein are methods and devices for non-invasive glucose measurement. In general, the methods of measuring glucose involve the use of a patch that is placed on the skin surface and secured thereon with an adhesive. A separate measurement device is placed adjacent to, or directly upon, the patch and is configured to interrogate the patch and measure the glucose collected therein. The measurement device is typically a small, hand-held device that is equipped with technology corresponding to that necessary to interrogate the patch. For example, the measurement device may take optical measurements or electrical measurements, depending upon how the detector in the patch is configured (e.g., when the detector is a fluorescent molecule, the measurement device will typically be configured to take optical measurements, when the detector is an electrochemical sensor, the measurement device is typically configured to make electrochemical measurements, and the like). The patch is configured so that only glucose correlatable to blood glucose (e.g., that glucose which has recently arrived on the skin surface via sweat) will be detected, while the remaining sources of glucose on the skin will not be detected.

Figure 1:
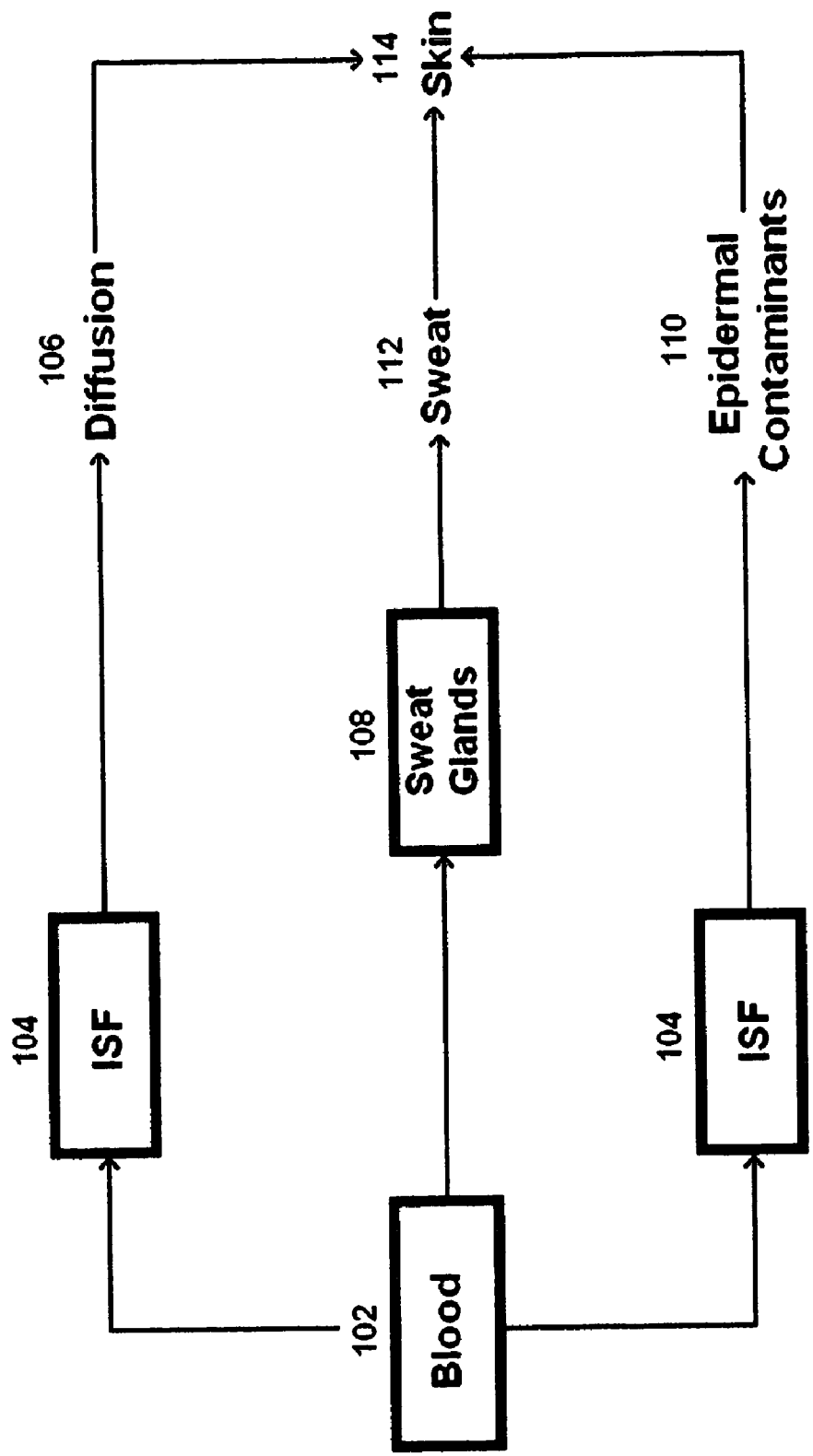
FIG. 1 provides a schematic of glucose transport mechanisms from the blood to the skin.

For example, as shown in FIG. 1, there are different routes by which the glucose in blood migrates to the skin over time. As shown there, the glucose in blood (102) passes to the interstitial fluid (104), or to sweat glands (108). After a period of time, the glucose levels in blood (102) and glucose levels in the interstitial fluid (104) reach equilibrium. In healthy subjects, this period of time is typically on the order of five to ten minutes. This relatively short time delay for equilibrium achievement between blood glucose and interstitial fluid glucose levels, has made interstitial fluid the focus of many efforts to develop continuous glucose monitoring technology.

Glucose derived from the interstitial fluid (104) is also transported by diffusion (106) through the stratum corneum to the skin surface. However, the relative impermeability of the stratum corneum, or alternatively, the high quality of the barrier function of intact stratum corneum tissue, results in significant time delays for the passage across the stratum corneum by transdermal diffusion. The glucose delivered to the skin surface by transdermal diffusion lags behind blood glucose by many hours making it unsuitable for medical diagnostic uses.

Glucose may also arrive on the skin surface via the process of stratum corneum desquamation resulting in epidermal contaminants (110), and the like. For example, epidermal glucose results from the specific enzymatic cleavage of certain lipids. This produces free glucose, a source of energy for the upper layers of the epidermis which are otherwise poorly perfused with blood. This free glucose is not representative of the corresponding blood glucose, or of the interstitial glucose values.

The sweat gland (108) may be considered a shunt that traverses the stratum corneum and allows rapid mass transport of material through an otherwise relatively impermeable barrier. Glucose from the interstitial fluid is the primary source of energy for the work-or-pump function of the eccrine sweat glands (108). The sweat secreted by the eccrine sweat gland contains a fraction of glucose from the blood (102), which erupts from the skin through tiny pores or orifices on the skin surface. We have discovered that a fraction of the secreted sweat may be re-absorbed by the stratum corneum. The amount of sweat, and consequently, the amount of glucose, back-absorbed into the stratum corneum depends on the hydration state of the skin and varies throughout the day. Thus, without blocking the back transfer of glucose from sweat into the stratum corneum, it may be difficult to develop an instrument that could correlate the glucose on the skin with that in the blood.

Cunningham and Young measured the glucose content in the stratum corneum using a variety of methods including serial tape stripping and aqueous extraction, and found approximately 10 nanograms per square centimeter per micron of depth of stratum corneum. See Cunningham, D. D. and Young, D. F., "Measurements of Glucose on the Skin Surface, in Stratum Corneum and in Transcutaneous Extracts: Implications for Physiological Sampling", *Clin. Chem. Lab Med*, 41, 1224-1228, 2003. In their experiments in collecting and harvesting glucose from the skin surface, Cunningham and Young found that the stratum corneum was the source of epidermal contaminants on the skin surface, and that these contaminants were not correlatable to blood glucose.

The glucose from epidermal contaminants typically reflects glucose abundance in the tissue anywhere from days to weeks prior to its appearance during desquamation (because epidermal turnover occurs approximately every 28 days). See, e.g, Rao, G., Guy, R. H., Glikfeld, P., LaCourse, W. R., Leung, L. Tamada, J., Potts, R. O., Azimi, N. "Reverse iontophoresis: noninvasive glucose monitoring in vivo in humans," Pharm Res, 12, 1869-1873 (1995). In a like manner, it is unlikely that the glucose brought to the skin surface via diffusion (106) can be correlated to blood glucose. In addition, because the glucose has to traverse the tortuous path of the skin layers to reach the surface, the glucose brought to the skin surface via diffusion often results in a lag time (e.g., in the range of a few hours to days), which is undesirable for purposes of glucose monitoring.

The methods and devices described herein provide a way to measure only that glucose brought to the skin via sweat. It should be understood that when reference is made to the term "skin" herein throughout, that term it is meant to include, not only the outermost skin surface, but also, the entire stratum corneum.

Methods of Use

As described briefly above, the methods provided here involve the use of a patch and a measurement device. Prior to application of the patch, the skin is wiped clean to remove any "old" or residual glucose remaining on the skin. The wipe is typically made of a material suitable for wiping the skin and comprises a solvent for removing glucose. For ease of description only, the term "wipe" will be used herein to include any type of fabric, woven, non-woven, cloth, pad, polymeric or fibrous mixture, and similar such supports capable of absorbing a solvent or having a solvent impregnated therein.

In some variations, the wipe contains a marker that is deposited on the skin. In these variations, the measurement device looks for the presence of the marker, and if the marker is detected, then the measurement proceeds. If the marker is not detected, the measurement does not proceed. In some variations, as will be described in more detail below, the measurement device provides an indication to the user that the skin has not been wiped. In this way, the possibility that a user obtains and relies upon a clinically dangerous measurement (e.g., based on an erroneous reading resulting from food residues or other glucose sources on the skin that are not correlated with the user's actual blood glucose) are minimized, and accurate measurements are facilitated. The marker may comprise a chemical having a short half-life, so that it will decay after a short period of time. In this way, a marker will only be valid for a single wipe, or a single use and erroneous detection of a marker on the skin surface will be minimized. In a like manner, the marker may also be bound to a volatile compound, and made to evaporate in a short period of time.

It should be noted however, that the wipe should not contain solvents, markers, or other chemicals that would interfere with the measurement of glucose. That is, a suitable glucose solvent would have the capacity to solubilize glucose without interfering with either the electrical or optical measurement of glucose. Polar solvents, and in particular, a mixture of distilled water and alcohol, have provided very good results in removing residual glucose from the skin surface. The ratio of distilled water to alcohol may be chosen such that there is sufficient water to dissolve the glucose, but not so much water as to make the removal of the excess water take an inconveniently long period of time relative to the measurement of glucose (e.g., more than 25 minutes). As noted above, it is desirable that the alcohol/water mixture, or other polar solvent, be selected such that it removes the residual glucose, but does not interfere with the glucose measurement.

After the skin has been wiped, a patch is placed on the skin. The patch may be placed on any suitable skin surface. For example, the patch may be placed on a finger, on the palm, on the wrist, etc. Typically, the patch is placed on the tip of the finger, because the fingertips have the greatest density of sweat glands. In addition, placement of the patch on the fingertip provides a convenient, discrete, and readily accessible site for testing. As will be described in more detail below, the patch comprises a collection layer, a detector, and an adhesive layer. The detector may be, for example, a dry, polymer-based electrochemical sensor, a wet electroenzymatic sensor in a microfluidic package, a glucose-sensitive fluorescent molecule or polymer, or the like.

A short period of time after applying the patch (e.g., from about 1 to about 25 minutes), the measurement device is placed adjacent to, or directly on, the patch. As shown in FIG. 2, patch (200) has been placed on the surface of fingertip (202). Measurement device (204) is placed adjacent to the patch (200) and interrogates (206) the patch. As noted briefly above, and as will be described in more detail below, the configuration of the measurement device is dependent upon the configuration of the patch. For example, if the patch detector is a fluorescent molecule, then the measurement device will be configured with the corresponding optics necessary to measure fluorescence. In some variations, the device and the patch are brought into contact with one another. For example, as will be described in more detail below, sometimes physical contact between the patch and the measurement device provides power to the device and/or is used to turn it on. Alternatively, the patch may comprise a battery source included therein.

After a measurement has been made, the user removes the patch and disposes of it. When it is desirable to once again measure glucose, the user wipes the skin, obtains a new patch, places the patch on a suitable and desirable location, and uses the measurement device to interrogate the patch. Alternatively, the user can interrogate the patch more than once, which may be useful for continuous measurements. For example, the patch could be interrogated several times within a time interval sufficient to allow the patch to refill with fresh sweat (while the old sweat is absorbed in the absorption layer). When an electrochemical-based detector is used, glucose can be measured as the difference between the second and first integrated electrical charges, for example. Similarly, when a fluorescent-based detector is used, the chemical equilibrium time constant should be small enough so that the fluorescent intensity can be used to measure the glucose in sweat.

Patches

The patches may be of any suitable configuration. For example, they may have a rectangular geometry, as shown in FIG. 3A, or they may have a circular geometry, as shown in FIG. 3B. The patch may also have a fun geometry, or include fun designs thereon (e.g., cartoons, shapes, dinosaurs, etc.), to entertain children, as shown in FIGS. 3C and 3D. The patch shown in FIG. 3A wraps around the fingertip, while the patches shown in FIGS. 3B, 3C, and 3D do not, and either variation is suitable. Similarly, the patch may be of any suitable size. For example, patches intended for the wrist will typically be larger than those intended for the fingertip. Making reference back to FIG. 2B, a patch (200) is shown there having a circular geometry and a diameter of 1 cm. Typically, circular patches intended for use on the fingertip will have diameters in the range of about 1.0 cm to about 2.5 cm, or areas ranging from about 0.785 $cm^2$ to about 4.91 $cm^2$. For placement of the patch on other skin surfaces, the patch may have areas ranging from about 2 $cm^2$ to about 10 $cm^2$.

Figure 4A:
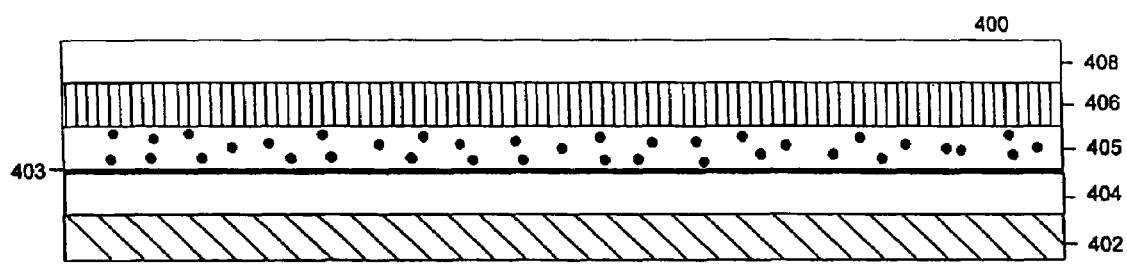
FIGS. 4A and 4B provide cross-sectional views of illustrative patches described herein.
Figure 4B:
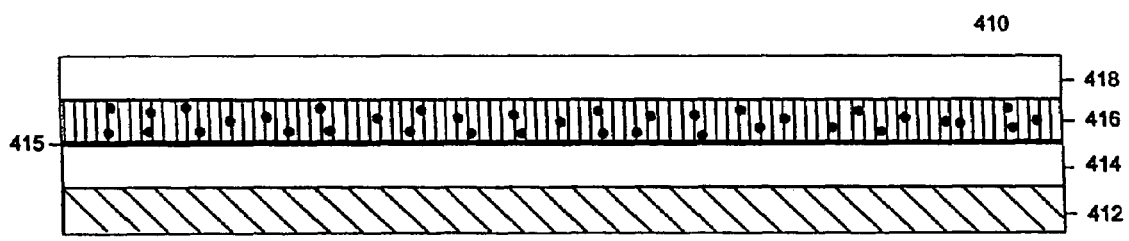

In some variations, and as generally shown throughout FIGS. 4A and 4B, the patch comprises an adhesive material, a collection layer, an interface layer, and a detector. However, in some variations, the patch does not comprise an adhesive material, and in these variations, the patch may be otherwise suitably adhered, held, or placed on the skin surface of a user. For example, the patch may be held on the skin surface by the user, or it may be held on the skin using an elastic material, medical tape, or the like. Similarly, in some variations, the patch does not comprise an interface layer. In these variations, the interface layer may be adhered to the measurement device, and the measurement device/interface layer may be placed onto the patch for a reading.

Making reference now to FIG. 4A, there is shown a cross-sectional view of patch (400) on skin (402). The patch (400) comprises an adhesive material in the form of a layer (404), a collection layer (405), a detection layer (406), and an interface layer (408). The detector need not be spatially separated in a distinct layer. For example, shown in FIG. 4B is a cross-sectional view of patch (410) on skin surface (412). Patch (410) comprises adhesive layer (414), collection layer (416), and interface layer (418). In the variation of FIG. 4B, the collection layer (416) contains the detector therein.

While not shown in the figures, the patch may also include at least one release liner. For example, a release liner on the bottom adhesive surface would protect the adhesive layer from losing its adhesive properties during storage and prior to use. Similarly, a release liner may be placed on top of the upper interface layer to protect the optical or electrical components contained therein. In some variations, no release liner is used and the interface layer is topped with a backing layer. In some variations, the backing layer is made from a woven or non-woven flexible sheet, such as those known in the art of transdermal patches. In other variations, the backing layer is made from a flexible plastic or rubber.

Typically the patch also comprises a sweat-permeable barrier as depicted by (403) and (415) in FIGS. 4A and 4B respectively. The sweat-permeable barrier is permeable to sweat, but acts as a barrier to epidermal contaminants, such as those contaminants brought to the skin surface via desquamation, and to non-correlatable glucose brought to the skin surface via diffusion. In this way, non-correlatable, and otherwise interfering glucose is not passed through to the collection layer for measurement. The sweat-permeable barrier may also aid in preventing or minimizing the re-absorption of glucose that has been brought to the skin surface via sweat, in the outer layer of the stratum corneum.

In general, the sweat-permeable membrane may comprise any material that allows sweat to pass therethrough, is non-toxic, and prevents reabsorption of the sweat into the skin. For example, the sweat-permeable membrane may be made of a hydrophobic coating or a porous hydrophobic film. The film should be thick enough to coat the skin, but thin enough to allow sweat to pass therethrough. Suitable examples of hydrophobic materials include petrolatum, paraffin, mineral oils, silicone oils, vegetable oils, waxes, and the like. While the sweat-permeable membranes depicted in FIGS. 4A and 4B are shown above the adhesive layers, they need not be. For example, in one variation, the sweat-permeable membrane comprises an oil and/or petrolatum coating applied to the skin surface. In this way, only that glucose that comes to the skin surface via the eccrine sweat gland will be detected. Similarly, a liquid polymer coating, or a liquid bandage may be used as a sweat-permeable membrane. Typically, these materials are liquid membranes with low surface tension, which leave openings over the sweat gland pores when they cure (e.g., silicon polymers such as SILGARD®). The liquid polymer coating has significant advantages in that it is impermeable to water everywhere except the sweat gland pores, but a solid polymer layer with micropores may also be used, for example the Whatman NUCLEOPORE® polycarbonate track-etch membrane filters. Other suitable membranes include the ANOPORE® inorganic membranes consisting of a high-purity alumina matrix with a precise non-deformable honeycomb pore structure.

It should be understood that although sweat-permeable membranes (403) and (415) are depicted in FIGS. 4A and 4B respectively as separate layers, they need not be. Indeed, in some circumstances, it may be desirable to combine an adhesive polymer with the liquid polymers described above. In this variation, the liquid polymer would begin to cure (or set up as a solid) when exposed to oxygen (e.g., when the release liner is removed). The layer would cover the epidermis, but would leave holes only over the sweat gland orifices. In this way, only glucose brought to the skin surface via the sweat glands would be passed through to the collection layer. As noted above, in addition to allowing glucose in sweat to transport to the skin surface, the sweat-permeable membrane may also be useful in blocking diffusion and in blocking the generation of epidermal debris resulting from desquamation. Accordingly, only the glucose from the sweat, which can be correlated with blood glucose, will be measured.

Figure 2B:
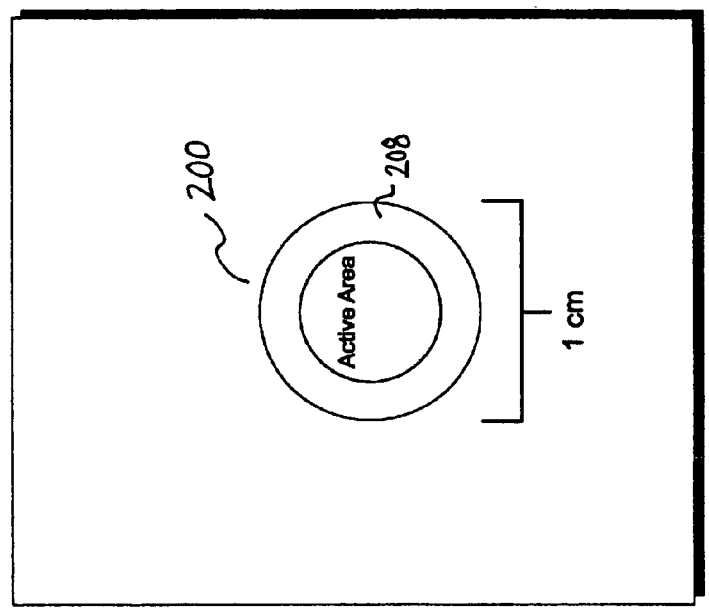
FIG. 2B provides an illustrative top view of one suitable patch.
Figure 2A:
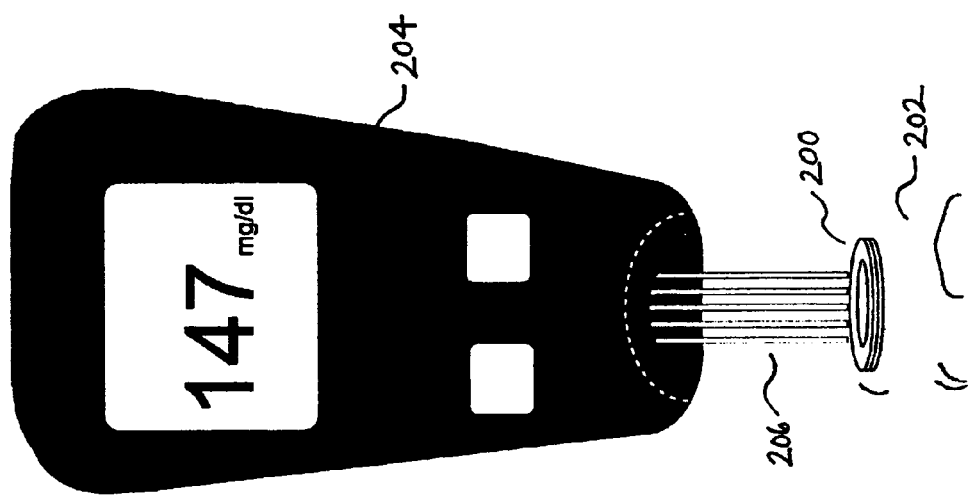
FIG. 2A provides an illustration of one suitable variation of how the devices and methods described herein may be used to measure glucose on the skin.
Figure 3:
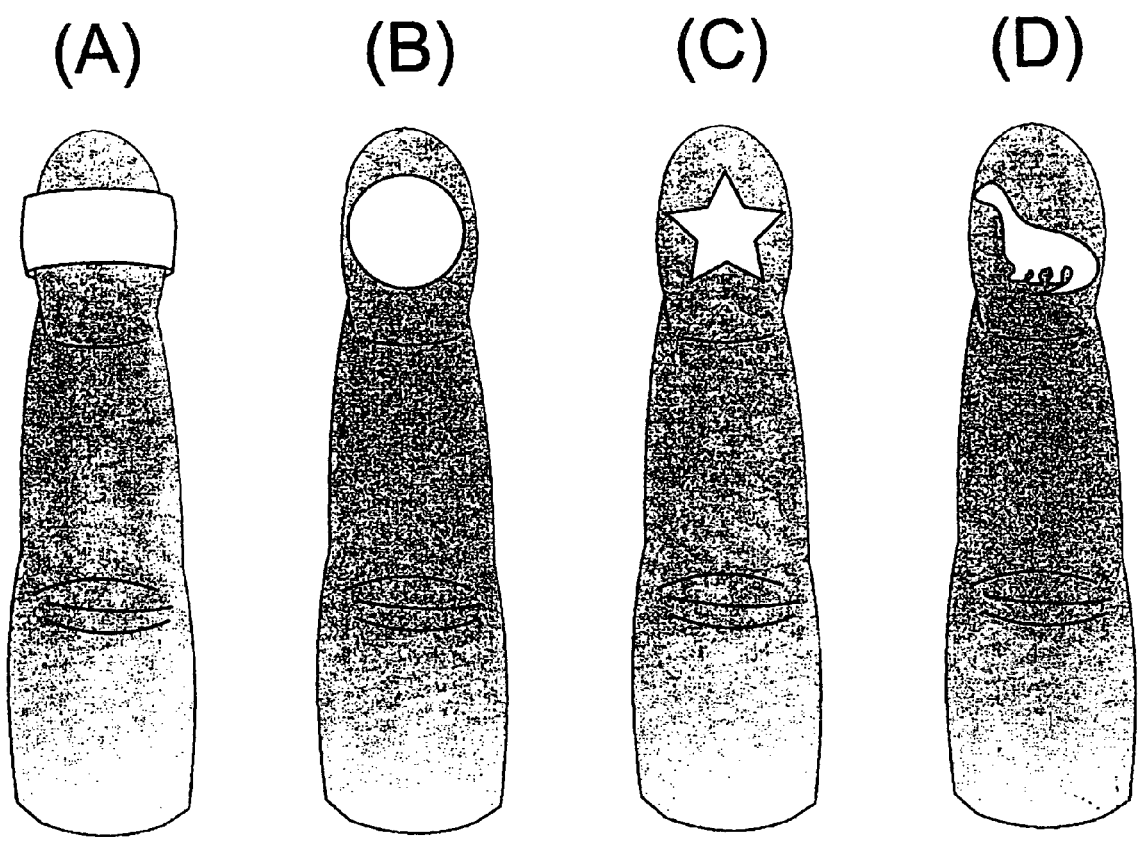
FIGS. 3A-3D depict several illustrative shapes for the patches described herein, and provide top view illustrations of how those patches may be worn by a user.

The adhesive material may comprise an annular overlay layer as depicted by (208) in FIG. 2B or it may comprise a layer of adhesive contemporaneous and coextensive with at least one other patch layer. Any suitable adhesive may be used. For example, common pressure sensitive adhesives known in the transdermal patch arts, such as silicone, polyacrylates, and the like, may be used. We note here that in some circumstances, it may be desirable to provide an adhesive layer, or an adhesive and sweat-permeable barrier combination layer, that is relatively dry. This is because it is thought that excessive wetting of the stratum corneum may inhibit sweat gland function (see, e.g., Nadel, E. R. and Stolwijk, J. A. J., "Effect of skin wettedness on sweat gland response," *J. Appl. Physiol.*, 35, 689-694, 1973). In addition, the excessive wetting of the skin may help aid the liberation of glucose on the skin, resulting from desquamation. Accordingly, it may be desirable to limit the aqueous or otherwise wet nature of the interface between the skin and the patch.

The patch may also comprise a component to induce sweat by physical, chemical, or mechanical methods. For example, in one variation, the patch comprises pilocarpine and a penetration or permeation enhancer to induce sweat chemically or pharmacologically. The use of a penetration enhancer can help increase the rate at which the pilocarpine enters the body and thereby, increase the onset of the enhanced sweat response. Examples of suitable permeation enhancers include, but are not limited to ethanol and other higher alcohols, N-decylmethylsulfoxide (nDMS), polyethylene glycol monolaurate, propylene glycol monolaurate, dilaurate and related esters, glycerol mono-oleate and related mono, di and trifunctional glycerides, diethyl toluamide, alkyl or aryl carboxylic acid esters of polyethyleneglycol monoalkyl ether, and polyethyleneglycol alkyl carboxymethyl ethers. Pilocarpine may also be driven into the skin using iontophoresis. The present inventors have shown that the infusion of pilocarpine into the skin using iontophoresis increases the amount of sweat by about 20 fold per unit area. Similarly, other chemicals may be introduced into the skin to increase the sweat response.

Figure 6:
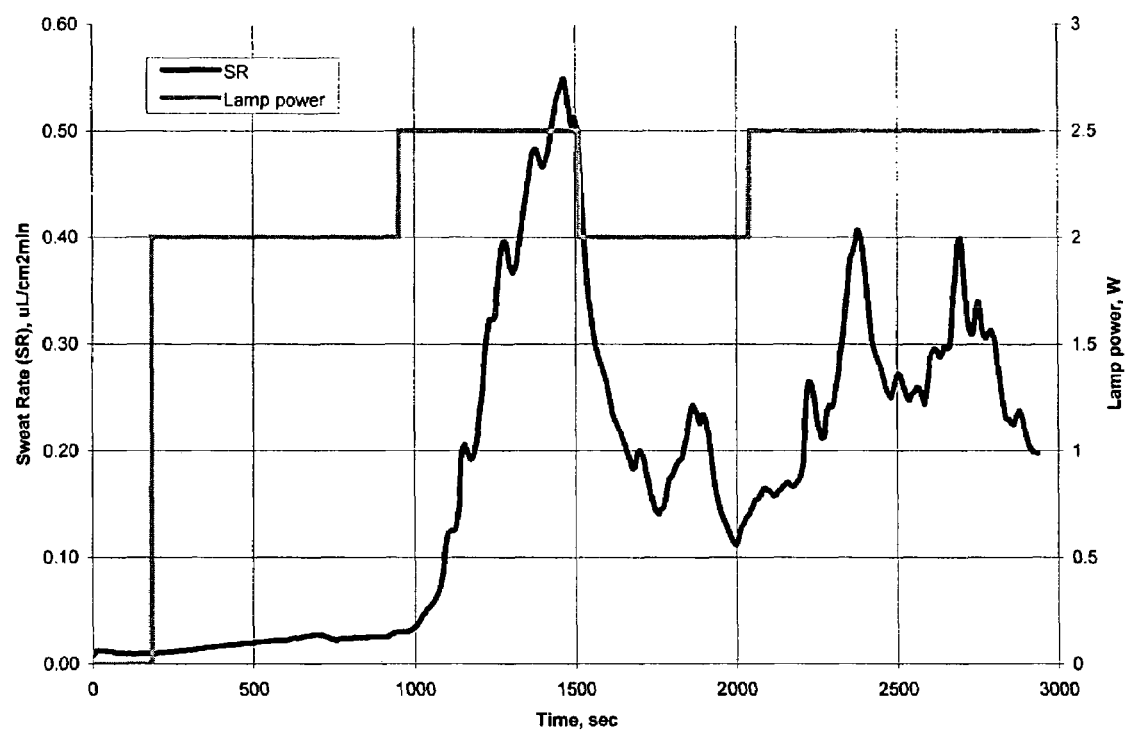
FIG. 6 shows the effect of thermal stimulation on the sweat response over time.

The patch may also comprise a component that increases the sweat response by initiating a local temperature increase. For example, a heater (e.g., an electrical resistance heater) may be used to increase the skin surface temperature and thus increase sweating. Thermal induction of a sweat response may also be achieved by the application of energy (e.g., in the visible or near infrared regions). For example, a lamp may be used to generate heat and induce sweating. Experiments were run to measure the sweat rate (in $\mu L/cm^2 \times min$) as a function of lamp power (W) versus time (sec). As shown by FIG. 6, there appears to be a minimum threshold required to induce a sweat response. In this instance, that threshold was in the range of about 2 to about 2.5 Watts (power to the lamp), when a MAGLITE®, Model LR00001, 6 Volt halogen lamp was used.

Direct electrical stimulation (i.e., Faradic stimulation) may also be used to induce a sweat response. Similarly, a chemical compound, or combination of compounds may be used to initiate a local temperature increase and therefore induce or increase the sweat response. For example, two chemical compounds may be used, separated by a thin membrane. The membrane may be removed by a pull-tab when the patch is adhered to the skin, thereby bringing the compounds into contact with each other, and causing an exothermic reaction. In this way, a source of heat is provided.

Physical mechanisms of inducing or increasing sweat may also be used. For example, in one variation, the measurement device is brought into contact with the patch and force is applied to the patch in a manner sufficient to cause an increase in the transport of sweat to the skin. The applied pressure over the collection patch results in fluid from the sweat gland lumen being expressed and delivered to the skin surface. In addition, the measurement device could include a suction or vacuum mechanism, which in combination with the applied pressure would result in a larger amount of sweat being delivered to the collection layer of the patch. Vibration may also be used to induce sweat.

Sweat may also be induced by the use of an occlusive layer within the patch, which inhibits evaporative loss from the skin surface and thereby permits a more efficient sweat accumulation into the patch collection layer. This occlusive layer may comprise an element within the patch, or may be a removable overlay which is separated from the patch prior to use of the measurement device. This occlusive layer may be, e.g., a thin polyvinyl film or some other suitable water vapor-impermeable material.

In some variations, it may be necessary to provide a method to minimize the effect of variable sweat rates on the amount of glucose accumulation in the collection layer. There are several ways in which the effect of variable sweat rates may be normalized by the method of collection or the use of various analytes. One method of minimizing the effect of a variable sweat rate is to normalize the flux of the measured glucose. For example, when glucose is transported to the skin surface by sweat, the total amount of glucose deposited on the unit of skin surface per minute can be calculated as follows:

$$GF = SR \times SG$$

where GF is glucose flux ($ng/cm^2 \times min$), SR is the sweat rate ($\mu L/cm^2 \times min$), and SG is the glucose concentration in sweat ($ng/\mu L$).

Often the sweat rate fluctuates over time as the result of physical or emotional stimulation, and this fluctuation can result in a variation in the amount of glucose collected from the skin surface, and hence the accuracy of the glucose concentration measurement. This variation can be significantly reduced if sweat rate is measured as a function of time and used to normalized the glucose flux, as follows:

$$GF/SR = (SR \times SG)/SR = SG$$

Figure 5A:
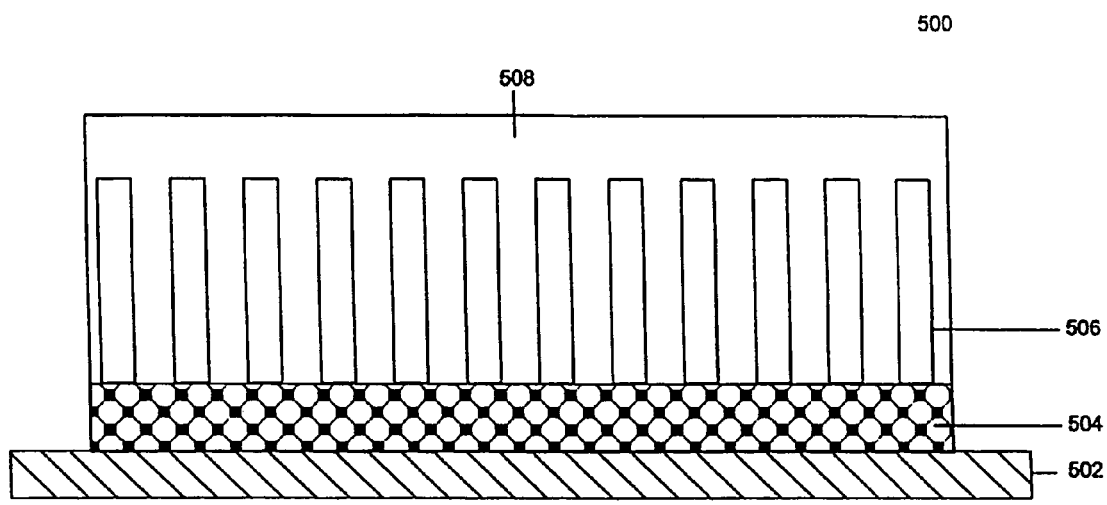
FIGS. 5A-5G show illustrative variations of how a fixed volume reservoir may be used with the patches described herein.
Figure 5B:
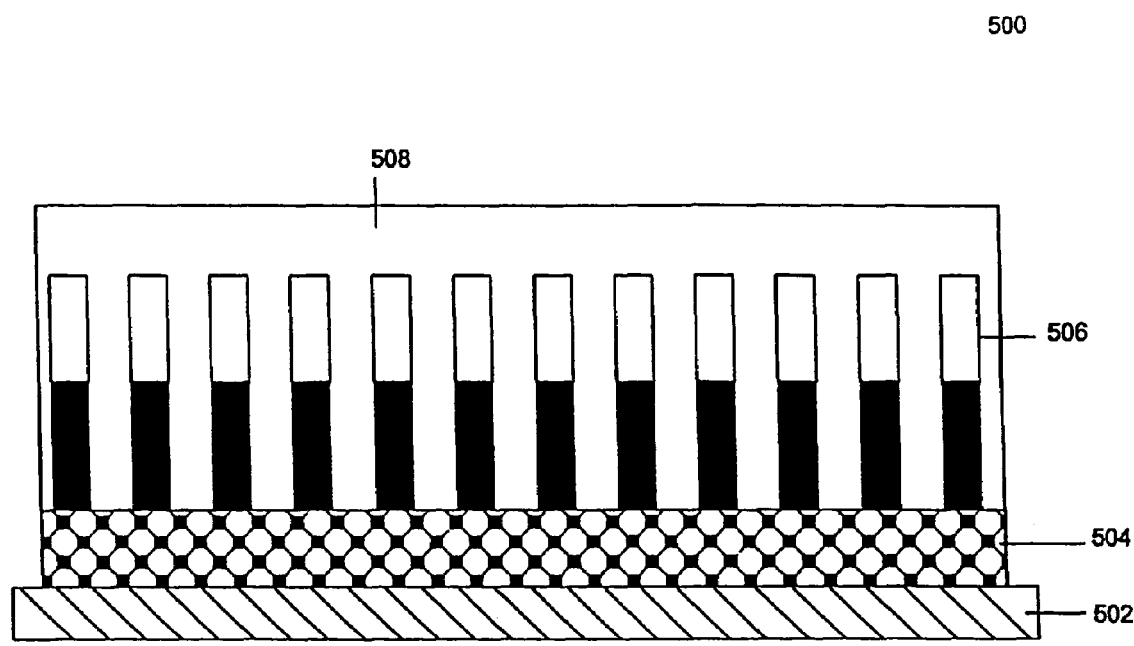

Another method, for example, may comprise configuring the collection layer of the patch to collect a constant volume of fluid so that a variable sweat rate affects only the time to fill the collection volume, but not the amount of fluid collected. For example, the collection layer may comprise an absorbent polymer that becomes saturated at a given volume of fluid. Similarly, the collection layer may comprise a capillary reservoir having a fixed volume. Suitable capillary reservoirs include those filters manufactured by Whatman described above. Shown in FIG. 5A is a patch (500) on skin surface (502). In this variation, the adhesive layer and the sweat-permeable membrane are combined in a single layer (504). Within the collection layer (508) is a fixed volume reservoir (506). The fixed volume reservoir (506) is shown in FIG. 5A as completely empty. As sweat begins to transport to the skin surface, and through the sweat-permeable membrane, the fixed volume reservoir begins to fill, as depicted in FIG. 5B.

Figure 5C:
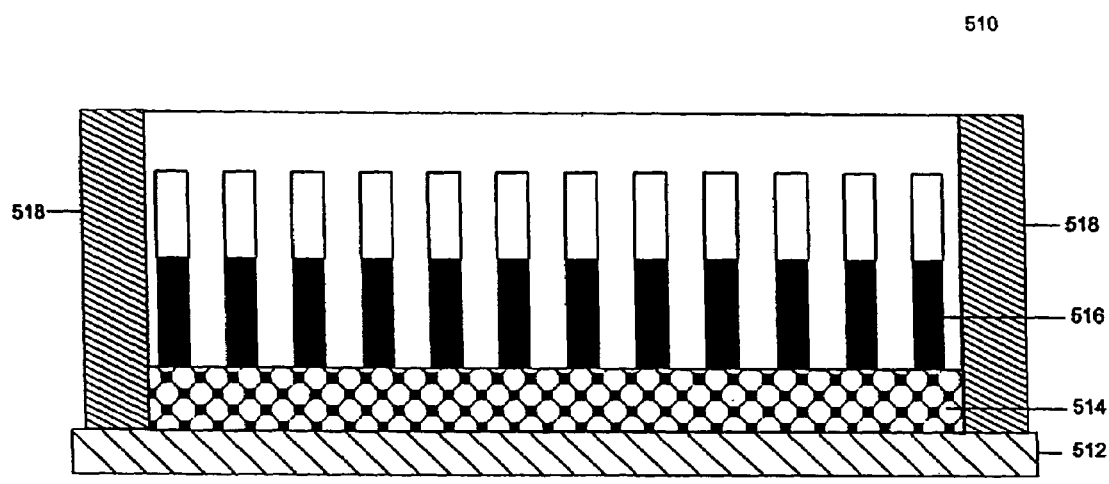
Figure 5D:
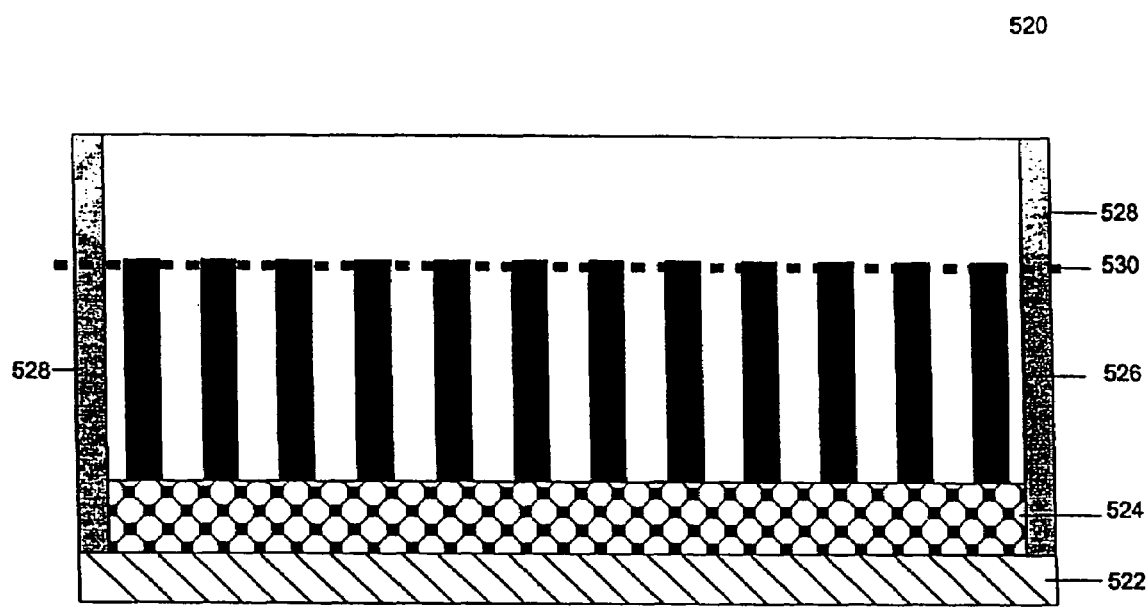
Figure 5E:
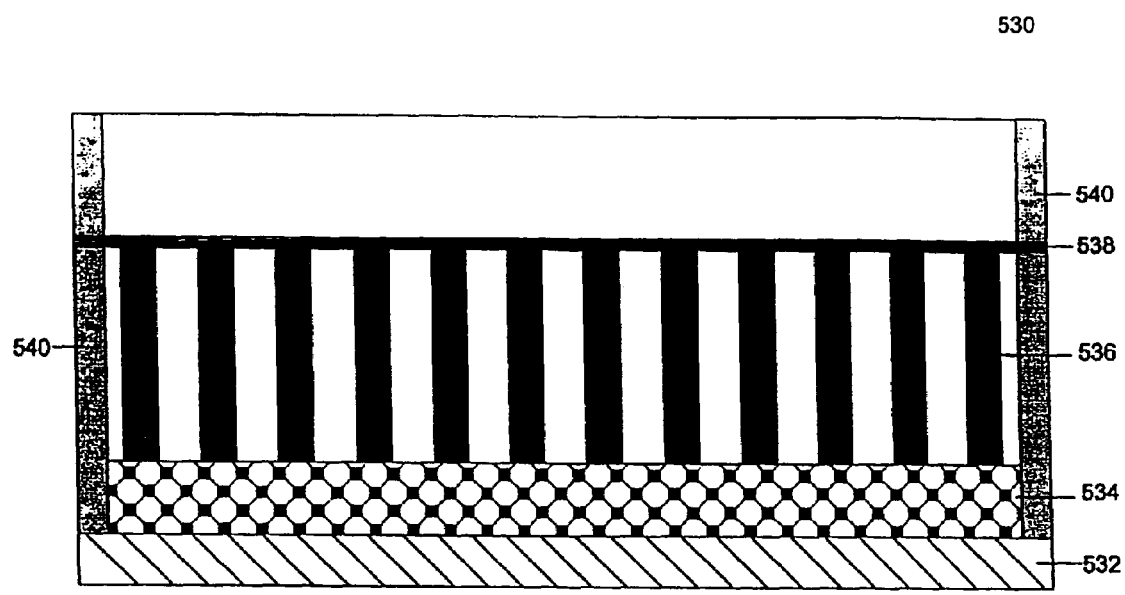

A number of different techniques may be used to determine when the fixed volume reservoir, and hence the collection layer is filled. For example, electrical capacitance, electrical conductance, or optical measurements may be used as shown in FIGS. 5C, 5D, and 5E respectively. For example, shown in FIG. 5C is patch (510) on skin surface (512). In this FIG., sweat has already passed through the adhesive and sweat-permeable membrane layer (514) to fill the fixed volume reservoir (516). Conductors (518) for forming a dielectric filled capacitor are placed on either side of the patch (510). In this way, the volume within the fixed volume reservoir (516) may be determined by a change in capacitance of the dielectric filled capacitor. Illustrative conductors suitable for use with the patches described herein include those made from silver, platinum, and the like.

Similarly, electrical conductance may be used to determine when the reservoir is filled. Shown in FIG. 5D is patch (520) on skin surface (522). Sweat has already passed through the adhesive and sweat-permeable membrane layer (524) to fill the fixed volume reservoir (526). A conducting circuit (530) is established with reservoir (526), here shown at the top of the reservoir. The circuit may be open or closed. In this way, the volume within the fixed volume reservoir (526) may be determined by a change in conductance (e.g., at the top of the reservoir). Supports (528) may be provided on either side of patch (520) to help provide structurally integrity thereto. These supports may be plastic substrates with suitably configured printed circuit elements that could provide a circuit path through the fixed volume reservoir. Changes in resistance or conductance at the top of the reservoir could indicate whether the fluid volume in the reservoir had reached a maximum. The modest power required to drive a current through the circuit described here could be provided by an inductive coupling mechanism enclosed within the measurement device, a plastic battery, and the like.

Optical transmission may also be used to determine when the reservoir is filled. Shown in FIG. 5E is patch (530) on skin surface (532). Sweat has already passed through the adhesive and sweat-permeable membrane layer (534) to fill the fixed volume reservoir (536). An optical transmission path (538) is established with reservoir (536), here shown at the top of the reservoir. In this way, the volume within the fixed volume reservoir (536) may be determined by a change in optical transmission (e.g., at the top of the reservoir). An optical fiber path could be provided at the top of the mechanical supports (540) on either side of patch (530) connecting an optical source on one side of the patch with an optical detector on the other. Changes in the measured transmission could indicate whether the fluid volume in the reservoir had reached a maximum. Power for the optical source and detector may be included in the measurement device.

Figure 5F:
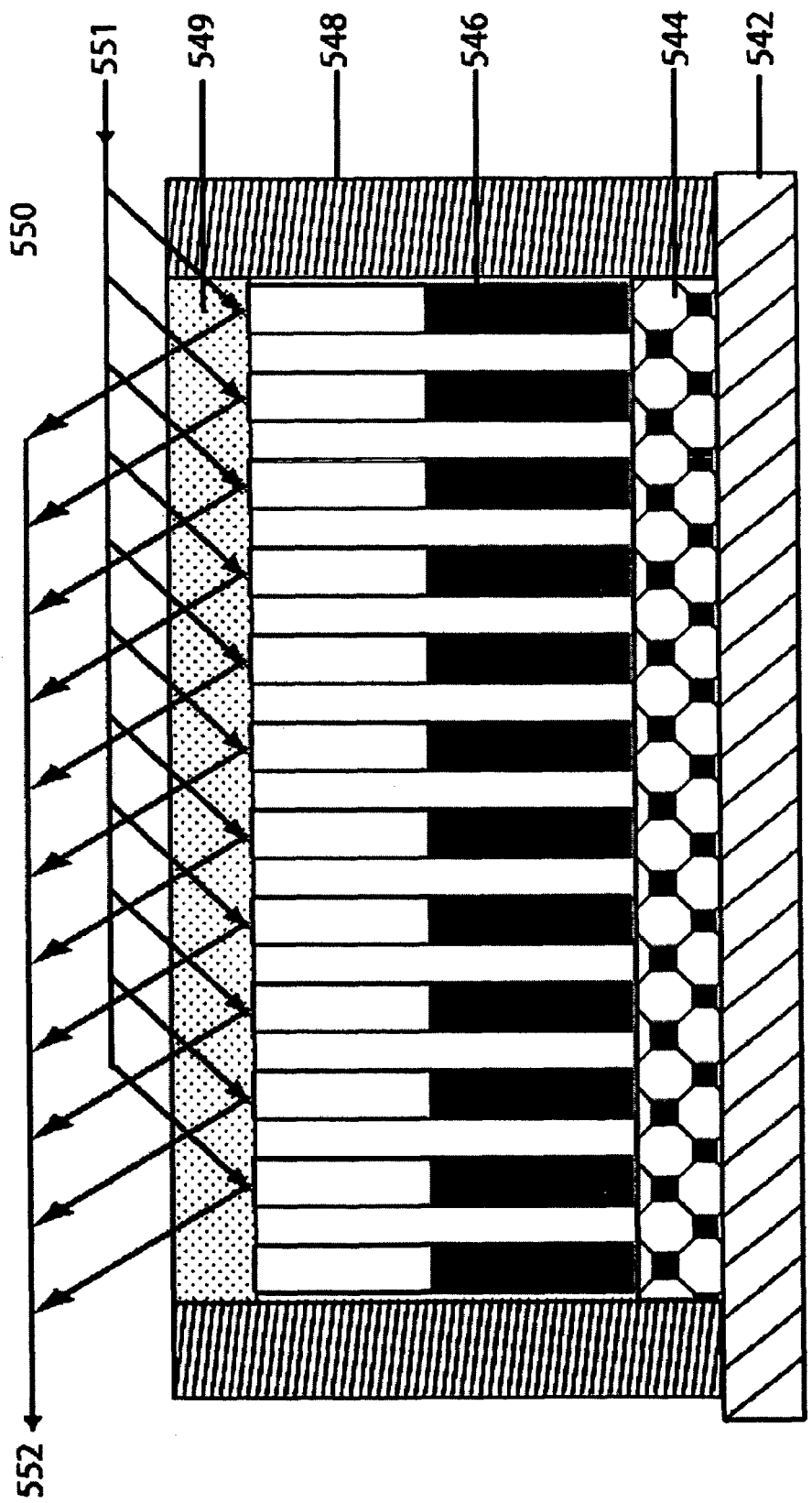
Figure 5G:
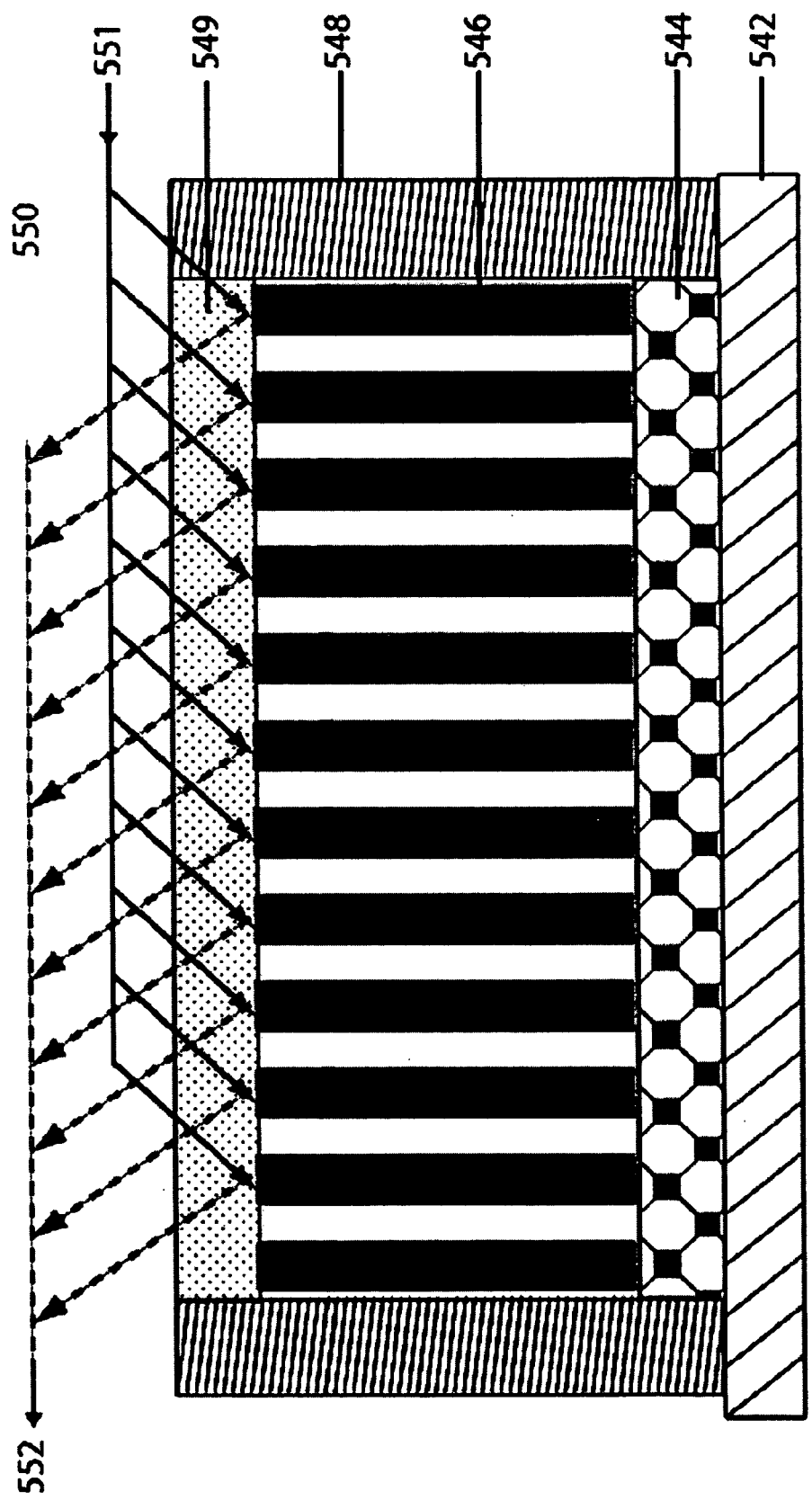

Optical reflection may also be used to determine when the reservoir is filled. For example, as shown in FIG. 5F is patch (550) on skin surface (542). Sweat has already passed through the adhesive and sweat-permeable membrane layer (544) and partially filled fixed volume reservoir (546). A transparent plate (549) is located on the top of the reservoir. This plate has an optical index of refraction close to that of sweat (about 1.33). Incident light (551) illuminates the interface between reservoirs (546) and plate (549). Here, the reflected light (552) has a high intensity because the optical index difference between the plate (549) and air (which has an optical index of refraction of about 1.0) is high. Shown in FIG. 5G is the same patch (550) where the reservoir (546) is completely filled with sweat. Here, the reflected light (552) has a low intensity because the optical index difference between the plate (549) and sweat is low (both have an optical index of refraction of about 1.33). Thus, the drop in reflected light intensity may be used as an indicator that the reservoir is full. An optical source and detector may be included in the measurement device and the patch can be interrogated via an optical interface.

The determination of glucose level in the patch may be normalized for variable sweat rates by the use of a non-glucose analyte specific to sweat that is constant in concentration (e.g., lactate, urea, sodium chloride, other electrolytes, etc.). In this way, the glucose concentration may be normalized to that value. For example, a separate chemical detector may be incorporated into the patch to independently determine the amount of the sweat analyte. The amount of this sweat analyte accumulated in the collection layer depends only on the volume of sweat in the layer. Once this is determined, the amount of glucose measured in sweat may be normalized to the total volume of sweat collected, thereby avoiding errors associated with measuring an increased accumulation of glucose in the collection layer of the patch (i.e., due to increased sweating rather than increased physiological glucose concentrations). Alternatively, there may be physiological markers in sweat that increase with increased sweat rate. Determination of the concentration of these markers may also serve as a method for normalization of the glucose accumulated in the collection layer.

As described above, the patch comprises a detector. The detector may be in its own layer, adjacent to the collection layer, or, depending on the nature of the detector, it may be combined in the collection layer itself. In the absence of thermal, emotional, physical, or pharmacological stimulation, typical values of sweat output on the volar forearm and fingertip are relatively small. Sweat output varies from one individual to the next and from one anatomical site on the body to another. The maximum sweat rate per gland has been reported to range from about 2 nL/min to about 20 nL/min. See Sato, K. and Dobson, R. L. "Regional and individual variations in the function of the human eccrine sweat gland," *J. Invest. Dermat.*, 54, 443, 1970. Assuming insensible perspiration rates per gland of 1 nL/min and using measured sweat gland densities at different parts of the body, a total sweat output can be estimated. Typical sweat gland densities on the forearm are approximately 100 glands per square centimeter, which give 0.1 µL sweat per square centimeter per minute. Typical sweat gland densities on the volar fingertip are approximately 500 glands per square centimeter, which give 0.5 µL sweat per square centimeter per minute. In the absence of stimulation, the number of active sweat glands per unit area is often reduced by one-half the total available. Boysen et al., described above, found that the glucose concentration in sweat was approximately one one-hundredth normal blood glucose values (e.g., 1 mg/dl). Hence the flux of glucose to the surface of the volar fingertip may be estimated to be in the range of from about 2.5 nanograms to about 5 nanograms per square centimeter per minute. Accordingly, the detector described here must be capable of detecting nanogram quantities of glucose (less than 100 nanograms) and the measurement device described herein must be capable of performing ultra-sensitive glucose measurements.

Indeed, we have demonstrated that the flux of glucose brought to the skin via sweat was on the order of 1-20 nanograms per square centimeter per minute in the absence of thermal, pharmacological or other forms of stimulation. These measurements were made using the Wescor MACRODUCT® (459 South Main Street Logan, Utah 84321) system and in specially adapted sweat collection chambers. Sweat collected in the Wescor MACRODUCT® and in the sweat collection chambers was then analyzed using a Dionex (Sunnyvale, Calif.) High Performance Anion Exchange with a Pulsed-Amperometric Detector (HPAE-PAD). The sensitivity and specificity of the HPAE-PAD system was tested using analytical samples. We detected glucose in amounts as low as 1 nanogram using HPAE-PAD.

Several types of suitably sensitive detectors may be used. For example, the detectors may be electrochemical-based, or may be fluorescent-based. Suitable electrochemical sensors may be those comprising an immobilized glucose-oxidase or other enzyme(s) in or on a polymer or other support, and those comprising glucose-oxidase or other enzyme(s) in a microfluidic configuration. Similarly, the detector may be fluorescent-based, for example, based on enhanced or suppressed fluorescence of a glucose-sensitive fluorescent molecule.

As noted above, any suitable electrochemical detector may be used. For example, the electrochemical detector may be polymer based, based on microfluidics, and the like. When the electrochemical detector is polymer based, the polymer is typically permeable to glucose, and a glucose-reactive enzyme is immobilized on or within the polymer. The interface layer comprises at least two electrodes, which are typically activated by the measurement device when it is brought into electrical contact with the patch. In one variation, the enzyme glucose oxidase is used, which produces hydrogen peroxide that reacts at the at least one electrode to produce a measurable electrical current proportional to the glucose concentration. That is, using an enzymatic process known in the art, the glucose oxidase catalyzes the reaction of glucose and oxygen to produce gluconic acid and hydrogen peroxide. The hydrogen peroxide is then electrochemically reduced at the at least one electrode, producing two electrons for detection. As noted above, electrical contact between the measurement device and the patch may also serve to provide power to the patch (although, as noted above, the patch may comprise a battery therein as well). The measurement device interrogates the patch (i.e., the detector) and provides a single discrete reading.

When microfluidics based electrochemical detectors are used, the patch typically comprises a fluid reservoir, a flow channel, a gating valve, and sensor electrodes. In this variation, the electrochemical enzyme is typically in solution. The interface layer comprises at least one electrode, which is activated by the measurement device when placed into electrical contact with the patch. As with the case above, electrical contact between the measurement device and patch, may serve to power the patch. A microfluidic sensor may also comprise a reservoir with a reference analyte to provide in situ calibration of the detector. As with the cases above, electrical contact between the measurement device and patch, may serve to provide power to the patch, or the patch may comprise a battery therein.

Sensitivity to these electrochemical detectors may be increased by increasing the temperature during the detection cycles, by increasing the length of the detection cycle, by increasing the area of the detector, by appropriately selecting the operating potential, and by the use of selective membranes to screen interfering substances such as ascorbic acid, uric acid, acetaminophen, etc. In addition, differential methods may be used where the glucose sample is measured in the presence and absence of a glucose-specific enzyme and the glucose concentration is determined from the difference between these two signals.

For example, sensitivity may be increased by heating the sensor solution from 25° C. to 40° C., and such temperature increase is unlikely to affect the enzyme activity of the glucose detector. See, e.g., Kriz, D, Berggre, C., Johansson, A. and Ansell, R. J., "SIRE-technology. Part I. Amperometric biosensor based on flow injection of the recognition element and differential measurements," *Instrumentation Science & Technology*, 26, 45-57 (1998). Similarly, sensitivity may be increased by increasing the area of the detector, since the detector current increases linearly with the area of the detector electrode. Extending the length of time over which the measurement may be made may also be used to increase the measured charge and hence, the overall sensitivity of the detector. Lastly, covering the electrode with size- and, or, charge-selective membranes can allow passage of hydrogen peroxide, for example, while excluding ascorbate, urate and other material, which can react directly with the sensor to produce a spurious signal. Suitable size-selective membranes, for example, include those made of polyurethane, polyethylene and other materials as well as charge-selective membranes made of polyethylsulfide, NAFION®, cellulose acetate, and other materials that can be used as interference-screening membranes for electrochemical detectors.

The detector may also be a fluorescent detector. In this variation, the interface layer of the patch is made of a material that is optically transparent at the relevant excitation and emission wavelengths for the particular fluorescent-based detector used by the patch. In this variation, the measurement device need not be brought into direct physical contact, because interrogation of the patch is achieved by optically coupling the device and patch, as illustratively depicted in FIG. 2A. The internal electronics of the measurement device may also be configured to record a maximum signal as it is passed over the patch, thereby reducing the need for proper static registration between the measurement device and the patch itself. The patch may also include a glucose-insensitive reference fluorescent molecule to provide a ratiometric, rather than an absolute intensity measurement. The addition of a reference molecule may also protect against a spurious signal originating at the emission wavelength of the fluorescent-based detector.

The fluorescent detector typically comprises a glucose-sensitive fluorescent molecule immobilized in a polymer or suitable solvent, and as described above, may be in a separate layer, or dispersed throughout the collection layer. Because the measurement device will be measuring the glucose at a specific wavelength, it is desirable that the materials used in the patch do not have fluorescence at, or substantially near, the wavelength of the fluorescent emission of the glucose transducer molecule. Similarly, it is often desirable that the sweat-permeable membrane in these variations be opaque so as to prevent autofluorescence from the skin.

Suitable fluorescent detectors for example may be those described in U.S. Pat. No. 6,750,311 to Van Antwerp et al, which section on fluorescent detectors is hereby incorporated by reference in its entirety. As described there, fluorescent detectors may be based on the attenuation in the fluorescence intensity of labeled lectins or boronate (germinate or arsenate) aromatic compounds. Suitable lectins include concanavalin A (Jack Bean), *Vicia faba* (Fava Bean), *Vicia sativa*, and the like. Such lectins bind glucose with equilibrium constants of approximately 100. See, Falasca, et al., *Biochim. Biophys. Acta.*, 577:71 (1979). The lectin may be labeled with a fluorescent moiety such as fluorescein isothiocyanate or rhodamine using commercially available kits. The fluorescence of the labeled lectin decreases with increasing glucose concentration.

Boronate based sugar binding compounds may also be used as the basis for the fluorescent detector. Glucose reversibly binds to the boronate group in these compounds. Boronate complexes have been described which transduce a glucose signal through a variety of means. See, Nakashima, et al., Chem. Lett. 1267 (1994); James, et al., *J. Chem. Soc. Chem. Commun*, 477 (1994); and James, et al., *Nature*, 374:345 (1995). These include geometrical changes in porphyrin or indole type molecules, changes in optical rotation power in porphyrins, and photoinduced electron transfer in anthracene type moieties. Similarly, the fluorescence of 1-anthrylboronic acid has been shown to be quenched by the addition of glucose. See, Yoon, et al., *J. Am. Chem. Soc.*, 114:5874 (1992).

The dye used in the above fluorescent-based detector may be, for example an anthracene, fluorescein, xanthene (e.g., sulforhodamine, rhodamine), cyanine, coumarin (e.g., coumarin 153), oxazine (e.g., Nile blue), a metal complex or other polyaromatic hydrocarbon which produces a fluorescent signal. Unlike previously described applications of these sensors, where the sensors are specially-designed for equilibrium-binding with a target analyte and for reversibility, the binding constant of the fluorescent-based detectors described here may be increased so as to further lower the limit of detection.

Measurement Device

The measurement device interrogates the patch to measure glucose. The device measures the total quantity of glucose present in a fixed volume, and then converts the glucose measurement into a concentration. In general, the measurement device typically comprises a display, to display data. The device may also include warning indicators (e.g., a word prompt, flashing lights, sounds, etc.) to indicate that a user's glucose levels are dangerously high or dangerously low. In addition, as described briefly above, the measurement device may also be configured to verify that a skin-cleaning procedure has been performed. For example, when wipes with a marker have been used, the marker remains on the skin surface. If the measurement device detects the marker, then the measurement proceeds. If the measurement device does not detect the marker, the measurement does not proceed. In one variation, the measurement device provides an indication to the user, that the skin surface must be cleaned prior to use (e.g., using a word prompt, colored or flashing lights, or various sounds). The measurement device may also comprise an iontopheric source, for example, to be used to help drive pilocarpine, or other molecules of interest into the skin.

The configuration of the measurement device is dependent on the configuration of the detector in the patch. For example, when the measurement device is to be used with an electrochemical detector, the measurement device provides an electrical contact with the interface layer, and is either powered by the electrical contact, or is powered by an independent power source (e.g., a battery within the patch itself, etc.). The measurement device also typically comprises a computer processor to analyze data. Conversely, when the measurement device is configured for fluorescence detection, the measurement device is configured to provide optical contact or interaction with the interface layer. In this variation, the measurement device also typically comprises a light source to stimulate fluorescence. In some variations, the measurement device comprises both the necessary electrical contacts and the necessary optics so that a single measurement device may be used with a patch having various configurations of patch layers (e.g., one layer comprising a fluorescent-based molecule, and another layer comprising an electrochemical detector).

The measurement device further comprises computer executable code containing a calibration algorithm, which relates measured values of detected glucose to blood glucose values. For example, the algorithm may be a multi-point algorithm, which is typically valid for about 30 days or longer. For example, the algorithm may necessitate the performance of multiple capillary blood glucose measurements (e.g., blood sticks) with simultaneous patch measurements over about a 1 day to about a 3 day period. This could be accomplished using a separate dedicated blood glucose meter provided with the measurement device described herein, which comprises a wireless (or other suitable) link to the measurement device. In this way, an automated data transfer procedure is established, and user errors in data input are minimized.

Once a statistically significant number of paired data points have been acquired having a sufficient range of values (e.g., covering changes in blood glucose of about 200 mg/dl), a calibration curve will be generated, which relates the measured sweat glucose to blood glucose. Patients can perform periodic calibrations checks with single blood glucose measurements, or total recalibrations as desirable or necessary.

The measurement device may also comprise memory, for saving readings and the like. In addition, the measurement device may include a link (wireless, cable, and the like) to a computer. In this way, stored data may be transferred from the measurement device to the computer, for later analysis, etc. The measurement device may further comprise various buttons, to control the various functions of the device and to power the device on and off when necessary.

Kits

Also described here are kits. The kits may include one or more packaged patches, either alone, or in combination with other patches, a measurement device, or instructions. In one variation, the kits comprise at least one patch having a fluorescent-based detector and at least one patch having an electrochemical-based detector. Typically the patches are individually packaged in sterile containers or wrappings and are configured for a single use. The kits may also include multiple patches containing a single type of detector.

In another variation, the kits comprise at least one patch, and at least one measurement device. The at least one patch may have a detector corresponding to the measurement capacity of the measurement device (e.g., a patch having an electrochemical-based detector with a measurement device configured to provide electrical contact) or the patch may have a detector that does not correspond to the measurement capacity of the measurement device. In some variations, the kits comprise patches having multiple types of detectors, and the measurement device is configured with both electrical and optical capabilities.

EXAMPLES

Example 1

Investigation of the Effects of a Sweat-Permeable Membrane

A standard pilocarpine iontophoresis was performed simultaneously on the clean dry skin of both arms of a 40 year old male type I diabetic. The skin was wiped after stimulation and a MedOptix Macrovial surface was applied within 1 min following the iontophoresis (the MedOptix Macrovial allows serial samples of sweat to be collected from the same site on the skin. It is made from a plate having a hole therethrough for contact with the skin surface. On the non-skin contacting side of the plate, a capillary tube connects the hole to a collection chamber or vial). A Vaseline-paraffin barrier material (acting as a sweat-permeable membrane) was applied to the site on the right arm before the MedOptix Macrovial was applied. Samples were collected every 10 minutes from the appearance of the first drop of sweat on the end of the MedOptix Macrovial. The subject came in with an initial blood glucose level of about 220 mg/dl, which then stabilized at about 175 mg/dl during the first 40 minutes of sample collection. The subject then drank 10 oz of COKE® producing a rise in blood glucose to about 300 mg/dL.

Figure 7:
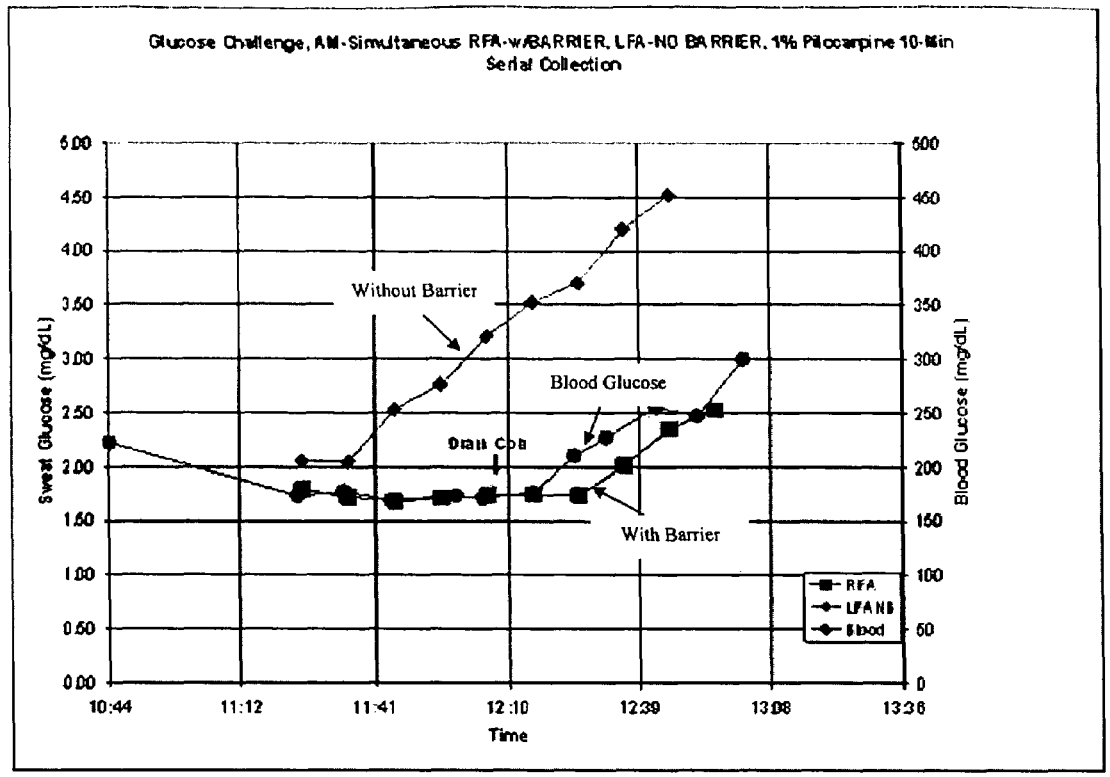
FIG. 7 shows the results of glucose measurements with and without the use of a sweat-permeable membrane.

The first two samples from the left arm (having no sweat-permeable membrane), contained approximately 2.0 mg/dl glucose. The glucose concentration of the sweat increased monotonically throughout the rest of the experiment to a maximum of approximately 5.0 mg/dl. This increase in concentration was not correlated to the increase in blood glucose, which began to rise 40 min after the initial rise in glucose in the left arm. In contrast, the glucose samples from the right arm, having the sweat-permeable membrane, remained flat at approximately 1.7 mg/dl and began to rise to a maximum of about 2.5 mg/dl about 10 min after the blood glucose started to rise. These results are shown in FIG. 7.

Figure 8:
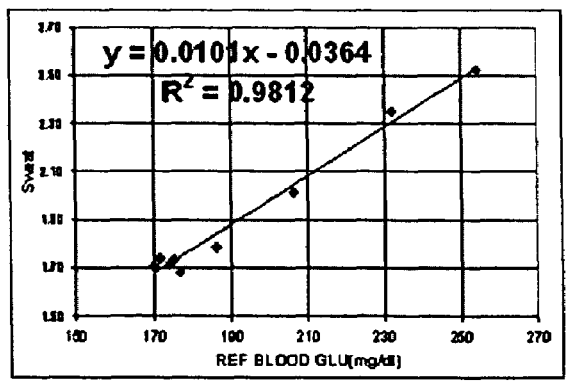
FIG. 8 demonstrates a normalized correlation between blood glucose and sweat glucose when a sweat-permeable membrane is used.
Figure 9:
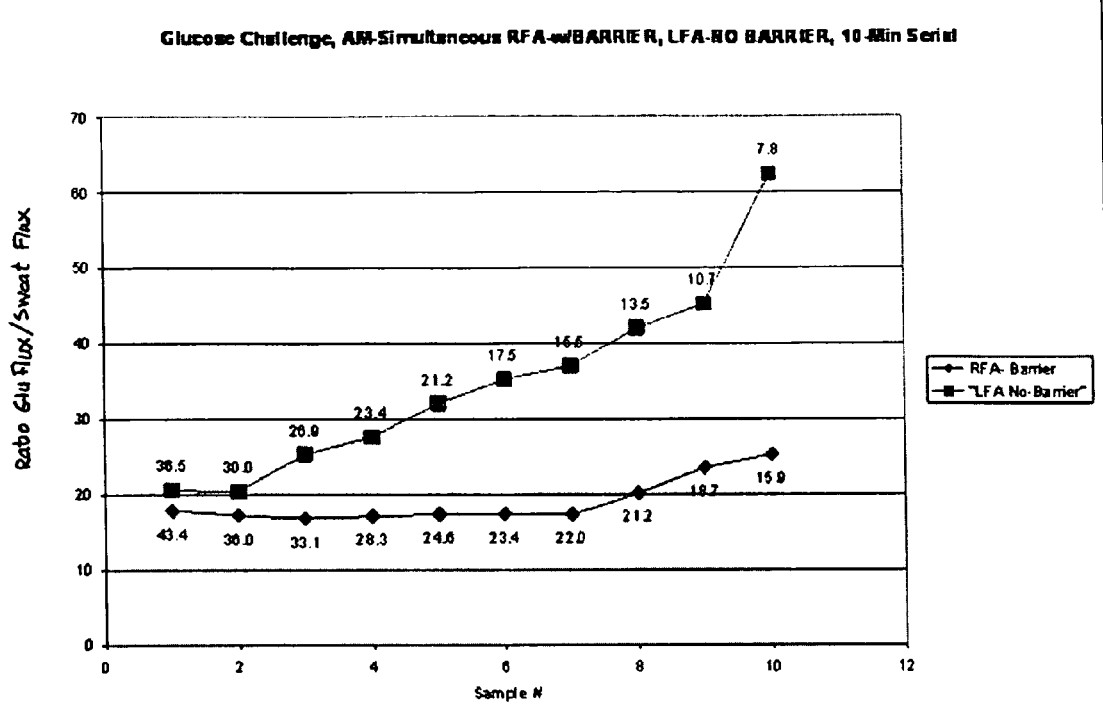
FIG. 9 is a plot of the ratio of sweat flux to glucose flux with and without a sweat-permeable membrane.

FIG. 8 shows a fit of blood glucose vs. sweat glucose for the site having the sweat-permeable membrane, which has been time-shifted. The blood and sweat glucose values were highly correlated, as shown by the $R^2$ of 0.98. The glucose concentration increased throughout the experiment on the site having no sweat-permeable membrane, which is consistent with a source of glucose independent of sweat. FIG. 9 is a plot of the ratio of sweat flux to glucose flux. As shown in that figure, in the case where there is a sweat-permeable membrane, the ratio remains constant while the blood glucose level is constant. Conversely, in the case where there is no sweat-permeable membrane, the ratio increases during this time. Accordingly, this data suggests that the use of a sweat-permeable membrane can act as a barrier to epidermal contaminants and glucose brought to the skin surface via diffusion.

Example 2

Correlation of Sweat Glucose to Blood Glucose

Both forearms of the subjects used were wiped with a standard 70% isopropyl alcohol swab. Cotton pads soaked in a buffered saline and 1% pilocarpine solution were applied respectively to the negative and positive electrodes of a standard iontophoresis device. A charge (dose) of 10 mA-min at a current of 1 mA was applied to the electrodes as they were held tightly against the skin of the subjects with elastic straps. The skin was wiped after 10 min of iontophoresis and a MedOptix Macrovial was applied to the site of the positive electrode within 1 min following the iontophoresis. Sample vials were replaced every 10 or 15 min until sweat flow became less than about 10 µl over the collection interval.

Blood glucose levels were determined from capillary finger pricks every 10 minutes using a commercial personal blood glucose meter (ACCU-CHECK ADVANTAGE®, Roche). In some experiments macro-vials were placed simultaneously on the right and left arms, while in others macro-vials were placed first on one arm and then after an hour on the opposite arm. Samples were filtered, diluted and analyzed on a DIONEX® HPAE-PAD system. The protocol varied with the initial state of the subject. For example, if the subject's blood glucose (BG) was high (>200 mg/dL) the subject was asked to follow his normal insulin program to lower BG. Otherwise, the subjects were given a drink containing 35-70 g of glucose at the start of the experiment to produce a rise in BG over the collection period.

Figure 10:
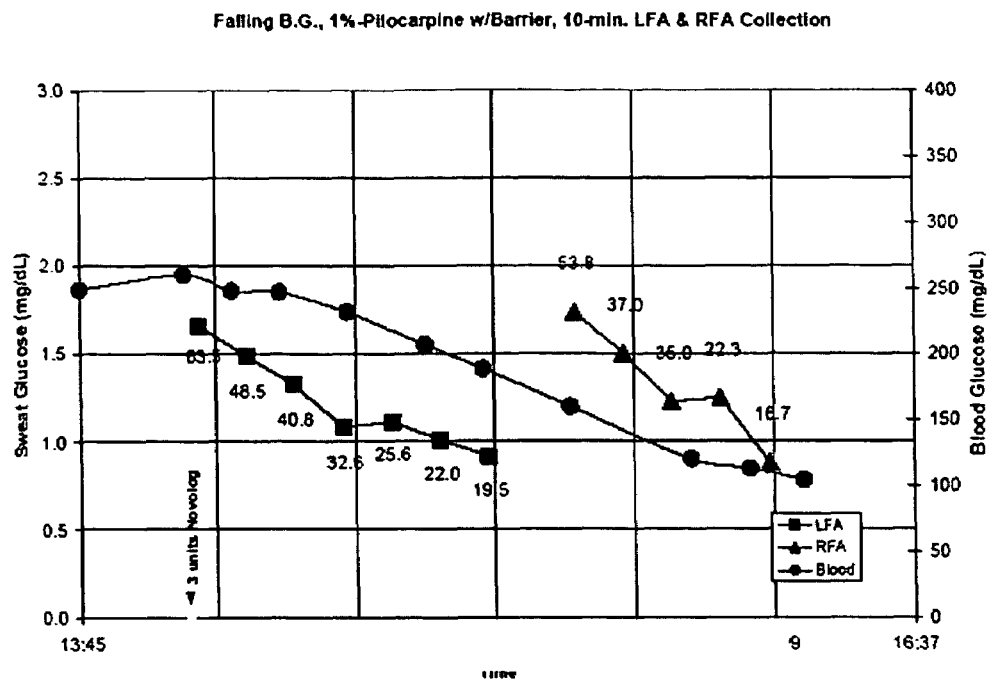
FIG. 10 is a plot demonstrating the sweat and blood glucose levels in a subject having falling glucose levels.
Figures 11A, 11B:
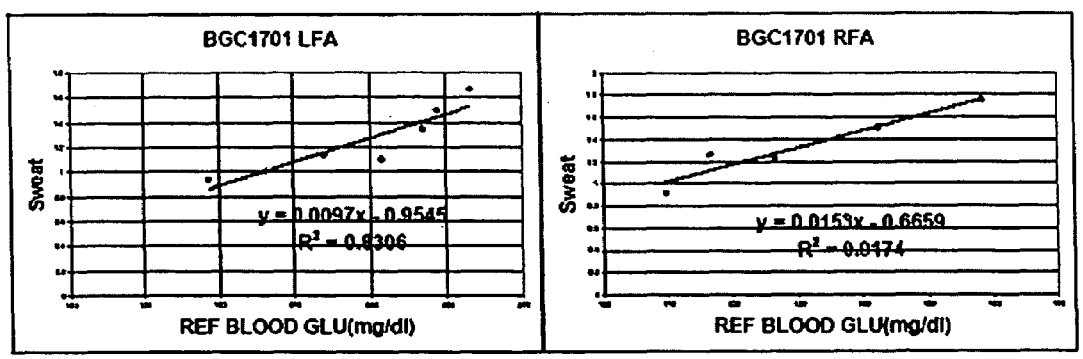
FIGS. 11A and 11B provide regression plots for the data plotted in FIG. 10.

Subject BCG1701, whose results are shown in FIGS. 10 and 11A-B, is a 48 year old female Caucasian, type II diabetic. Subject BDW2002, whose results are shown in FIGS. 12 and 13A-B, is a 39 year old male Asian, non-diabetic.

FIG. 10 shows a typical result for a falling BG. In this experiment the subject arrived with a high (250 mg/dL) BG level. Following the subject's own treatment regime, insulin was injected and samples of sweat and blood were collected from both the left and right forearms. The data shown in FIG. 10 is uncorrected for the offset some subjects demonstrate between their left and right arm. In this figure the BG (circles) decreases from 250 to 100 over the 2.5 hr experiment. The sweat glucose (SG) level is shown for the left forearm (LFA) followed by the right forearm (RFA). The numbers over the SG points give the volume in μl of sweat collected for each sample over the collection interval. FIGS. 11A and 11B show a linear regression plot of interpolated blood glucose vs. sweat glucose for the LFA and RFA respectively. These fits have $R^2$ values of 0.83 and 0.92, indicating a high degree of correlation between blood and sweat glucose levels.

Figure 12:
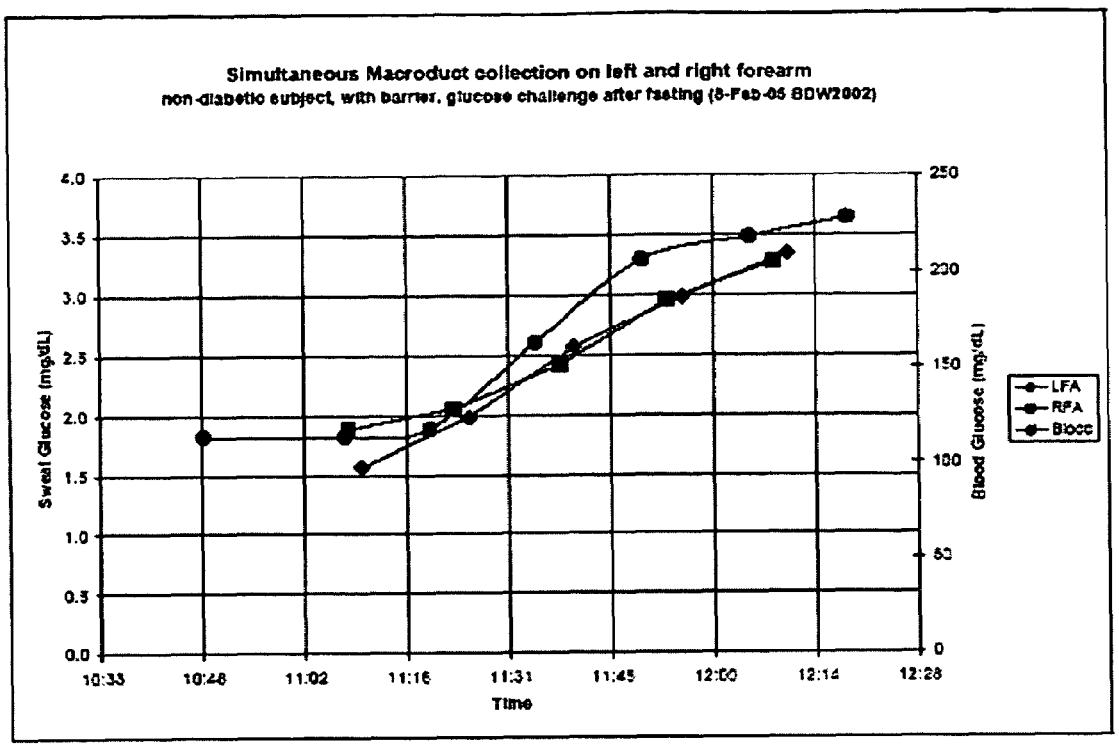
FIG. 12 is a plot demonstrating the sweat and blood glucose levels in a subject having rising glucose levels.
Figures 13A, 13B:
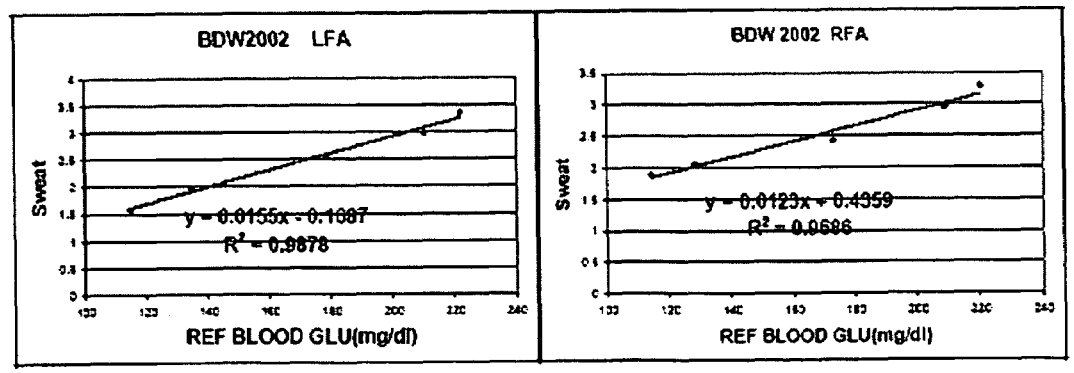
FIGS. 13A and 13B provide regression plots for the data plotted in FIG. 12.

FIG. 12 shows experimental results for an experiment with increasing BG. In this experiment the subject was given 75 g of glucose which raised his BG from about 125 to about 200 mg/dL over the course of the experiment. The data plotted in FIG. 12 shows the sweat glucose levels (left axis) of "simultaneous" collections of the LFA and RFA together with the changing blood levels (right axis). FIGS. 13A and B show plots of the linear regression of blood vs. sweat glucose for the LFA and RFA. The $R^2$ values were 0.99 and 0.97 for LFA and RFA respectively demonstrating a strong correlation between blood and sweat glucose in this experiment.

What we claim is:

1. A skin patch for use with a glucose measurement device comprising:
    an adhesive material;
    a collection layer for collecting sweat;
    a sweat-permeable membrane configured to act as a barrier to epidermal contaminants and as a barrier to glucose brought to a skin surface via diffusion when the skin patch is in contact with the skin surface, wherein the sweat-permeable membrane comprises a liquid polymer that cures when exposed to oxygen and that is adapted to leave openings over sweat gland pores on the skin surface upon curing;
    a detector configured to detect nanogram quantities of glucose in sweat; and
    an interface layer.

2. The skin patch of claim 1 wherein the detector is an electrochemical detector.

3. The skin patch of claim 1 wherein the detector is a fluorescent detector.

4. The skin patch of claim 1 wherein the sweat-permeable membrane comprises a material that is generally occlusive, but allows sweat to pass therethrough.

5. The skin patch of claim 1 wherein the sweat-permeable membrane and the adhesive material are in a single layer.

6. The skin patch of claim 1 wherein the sweat-permeable membrane comprises an inorganic material with micropores.

7. The skin patch of claim 1 wherein the sweat-permeable membrane comprises a solid polymer with micropores.

8. The skin patch of claim 1 further comprising a backing layer.

9. The skin patch of claim 8 wherein the backing layer is occlusive.

10. The skin patch of claim 1 further comprising a release liner.

11. The skin patch of claim 1 wherein the collection layer further comprises a fixed volume reservoir.

12. The skin patch of claim 11 further comprising an electric circuit through the fixed volume reservoir.

13. The skin patch of claim 11 further comprising at least two conductors.

14. The skin patch of claim 11 further comprising an optical transmission path through the fixed volume reservoir.

15. The skin patch of claim 1 wherein the interface layer comprises at least one electrode.

16. The skin patch of claim 1 wherein the interface layer is optically transmissive.

17. The skin patch of claim 1 further comprising pilocarpine.

18. The skin patch of claim 17 further comprising a penetration enhancer.

19. The skin patch of claim 1 further comprising a chemical capable of inducing a local temperature increase.

20. The skin patch of claim 1 further comprising a heater.

21. The skin patch of claim 1 further comprising a fluorescent-based reference molecule.

22. The skin patch of claim 1 further comprising a detector for detecting a non-glucose sweat based analyte.

23. The skin patch of claim 1 further comprising a battery.

24. A glucose measurement kit comprising:
    the patch of claim 1; and
    instructions for using the patch.

* * * * *